(12) United States Patent
Kurtz

(10) Patent No.: US 9,833,325 B2
(45) Date of Patent: Dec. 5, 2017

(54) TOTAL KNEE ARTHROPLASTY SYSTEM AND METHOD

(71) Applicant: William B. Kurtz, Nashville, TN (US)

(72) Inventor: William B. Kurtz, Nashville, TN (US)

( * ) Notice: Subject to any disclaimer, the term of this patent is extended or adjusted under 35 U.S.C. 154(b) by 0 days.

(21) Appl. No.: 14/993,482

(22) Filed: Jan. 12, 2016

(65) Prior Publication Data

US 2016/0120651 A1 May 5, 2016

Related U.S. Application Data

(63) Continuation of application No. 13/873,729, filed on Apr. 30, 2013, now Pat. No. 9,237,952.

(60) Provisional application No. 61/640,703, filed on Apr. 30, 2012, provisional application No. 61/781,626, filed on Mar. 14, 2013.

(51) Int. Cl.
*A61F 2/38* (2006.01)
*A61B 17/15* (2006.01)
*A61B 17/84* (2006.01)
*A61F 2/30* (2006.01)

(52) U.S. Cl.
CPC .......... *A61F 2/389* (2013.01); *A61B 17/157* (2013.01); *A61B 17/842* (2013.01); *A61F 2002/3013* (2013.01); *A61F 2002/30688* (2013.01)

(58) Field of Classification Search
CPC .......... A61F 2/38; A61F 2/3868; A61F 2/389; A61F 2002/4205

USPC ............................................ 623/20.32–20.34
See application file for complete search history.

(56) References Cited

U.S. PATENT DOCUMENTS

| | | | | |
|---|---|---|---|---|
| 5,387,241 | A * | 2/1995 | Hayes | A61F 2/30734 623/20.16 |
| 7,651,509 | B2 * | 1/2010 | Bojarski | A61B 17/0401 606/139 |
| 8,343,227 | B2 * | 1/2013 | Metzger | A61F 2/3836 623/13.12 |
| 2002/0129820 | A1 * | 9/2002 | Ryan | A61F 2/2445 128/858 |
| 2003/0130694 | A1 * | 7/2003 | Bojarski | A61B 17/0401 606/228 |
| 2003/0130695 | A1 * | 7/2003 | McDevitt | A61B 17/0401 606/232 |
| 2004/0049284 | A1 * | 3/2004 | German | A61F 2/30734 623/20.15 |
| 2004/0107000 | A1 * | 6/2004 | Felt | A61B 17/562 623/20.32 |
| 2010/0305709 | A1 * | 12/2010 | Metzger | A61F 2/3868 623/20.27 |

* cited by examiner

*Primary Examiner* — Anu Ramana
(74) *Attorney, Agent, or Firm* — Brainspark Associates, LLC

(57) ABSTRACT

Disclosed herein are prosthesis, surgical tools, and methods to preserve one or more ligaments of the knee by cutting a least a portion of natural bone during joint surgery, with a portion of the natural bone retained along with the natural attachment of an associated soft tissue structure. The natural bone portion with the associated soft tissue may be re-secured to relevant anatomy during or after knee surgery, which may include retention by features of a tibial prosthesis.

7 Claims, 20 Drawing Sheets

-- PRIOR ART --

-- PRIOR ART --

TOTAL KNEE ARTHROPLASTY SYSTEM AND METHOD

CROSS-REFERENCE TO RELATED APPLICATIONS

This application is a continuation of U.S. patent application Ser. No. 13/873,729 filed Apr. 30, 2013, entitled "Total Knee Arthroplasty System and Method," which in turn claims the benefit of U.S. Provisional Patent Application Ser. No. 61/640,703 entitled "Total Knee Arthroplasty System and Method," filed Apr. 30, 2012, and U.S. Provisional Patent Application Ser. No. 61/781,626 entitled "Total Knee Arthroplasty System and Method," filed Mar. 14, 2013. The disclosures of each of these documents is incorporated by reference in their entireties.

TECHNICAL FIELD

The invention relates to improved orthopedic implants, as well as related methods, designs, systems and models. More specifically, disclosed herein are improved methods, designs and/or systems for joint implant components that facilitate retention and/or repair of connective and/or soft tissues during a joint replacement procedure, including preservation of the anterior cruciate ligament (ACL).

BACKGROUND OF THE INVENTION

When a patient's knee is severely damaged, such as by osteoarthritis, rheumatoid arthritis, or post-traumatic arthritis, it may be desirous to repair and/or replace portions or the entirety of the knee with a total or partial knee replacement implant. Knee replacement surgery, also known as knee arthroplasty, can help relieve pain and restore function in injured and/or severely diseased knee joints, and is a well-tolerated and highly successful procedure. Where a total joint replacement is needed, it is often performed by a surgeon via an open procedure.

In an open procedure, the surgeon typically begins by making an incision through the various skin, fascia, and muscle layers to expose the knee joint and laterally dislocating the patella. The anterior cruciate ligament is often excised (if not already damaged or severed), and the surgeon will selectively sever or leave intact the posterior cruciate ligament—depending on the surgeon's preference and the condition of the PCL. Next, various surgical techniques are used to ablate, remove, shape or otherwise prepare the arthritic joint surfaces, and the tibia and femur are exposed for preparation and resection to accept various implant components.

It is well known in the art that knee arthroplasty involves the removal of one or more of the ligaments connecting the femur and the tibia. Often the normal function of one or more of the ligaments is severely compromised due to the deterioration or injury of the knee joint. One of the main purposes of a knee implant is to recreate the normal function of these removed ligaments. During this process, the ACL is almost always resected unless the surgeon chooses to use both a medial and lateral uni-compartment replacement. Meanwhile, the posterior cruciate ligament (PCL) is preserved in only about half of knee replacements performed.

Once the underlying bony anatomical support structures have been prepared, both the tibia and femur will typically receive an artificial joint component made of metal alloys, high-grade plastics and/or polymers to replace native anatomy and desirably function as a new knee joint. In the case of tibial implant components, the artificial joint can include a metal receiver tray that is firmly fixed to the tibia. In many cases, the tibial implant further includes a medical grade plastic insert (i.e. it may also be known as a "spacer" or "liner") that can be attached to the tray and positioned between the femoral component(s) and the tibial tray to create a smooth gliding surface for articulation of the components. Such a system can also allow for inserts of multiple sizes and/or thicknesses, which facilitates in-situ balancing of the knee as well as allowing the placement of inserts of differing designs and/or shapes.

Various surgical procedures in the past have sought to retain connective knee tissues during joint repair and/or replacement, but such techniques and associated implant designs have not gained widespread clinical acceptance for a variety of reasons. See, for example, U.S. Pat. No. 4,207,627 to Cloutier, entitled "Knee Prosthesis" filed Jun. 17, 1980, and J. M. Cloutier, *Results of Total Knee Arthroplasty With A Non-Constrained Prosthesis*, 65 J. BONE JOINT SURG. AM. 906 (1983); J. M. Cloutier et al., Total Knee Arthroplasty with Retention of Both Cruciate Ligaments: A Nine to Eleven-Year Follow-Up Study, 81-A J. BONE JOINT SURG. AM. 697 (May 1999); Nowakowski A M, et al. *Investigating the primary stability of the transversal support tibial plateau concept to retain both cruciate ligaments during total knee arthroplasty*. J Appl Biomater Biomech. 2012 Mar. 30:0; and Ries, M D, *Effect of ACL sacrifice, retention, or substitution on kinematics after TKA*. Orthopedics. 2007 August; 30 (8 Suppl):74-6.

While the implantation of total knee implant components via open procedures is a well-accepted procedure that is well tolerated by patients and has a high success rate, surgeons often prefer to minimize the disruption and/or removal of hard and soft tissues except where absolutely necessary. For example, the use of minimally-invasive and/or less-invasive surgical procedures has become increasingly prevalent, as such procedures are often associated with faster patient healing times and less scarification of the patient's anatomy. Moreover, where portions of a patient's existing anatomy, such as an ACL or PCL, are substantially intact and/or functional in the damaged knee, many surgeons would prefer to maintain the integrity of these structures during the surgical implantation procedure, as such structures can greatly contribute to the ultimate stability and/or performance of the treated anatomy. Unfortunately, many current implant designs require the removal of such structures, even where such structures are fully functional, in order to accommodate the implant components.

BRIEF SUMMARY OF THE INVENTION

There is a need in the art for joint replacement implant components, tools and associated procedures that facilitate the retention and/or repair of anatomical structures such as the ACL and/or PCL (and/or other relevant hard and/or soft tissue structures) during knee arthroplasty procedures.

It is an object of various exemplary embodiments of the present invention to overcome at least some of the disadvantages mentioned above associated with prior art devices and surgical procedures. The present invention provides an improved knee replacement system comprising novel tibial prostheses, novel bone-cutting instruments, and improved surgical techniques and methods for knee arthroplasty. The present invention is an improvement over the prior art because it allows for the preservation of the anterior cruciate ligament (ACL) and/or posterior cruciate ligament (PCL) in a total knee arthroplasty. In various embodiments, the ACL attachment remains affixed to a native tibial bone block, which can improve the normal kinematics of the knee joint.

The various embodiments described herein include implant components suitable for use in a patient's knee, including multi-component systems incorporating tibial trays, inserts, tools, methods, techniques and various devices that facilitate the preservation and/or repair of the ACL and PCL of a patient. Preservation of the ACL and/or PCL of a patient may improve physiological function and/or motion of the knee. Various other embodiments enable the retention of anatomical structures that can facilitate the surgical repair of various hard and/or soft tissues, including connective tissues such as the ACL and/or PCL of a patient. The joint replacement implant may be a standard implant, a modular implant and/or a patient-specific or adapted implant, including patient-specific implants and surgical tools created using preoperative image data of the patient's anatomy.

In various exemplary embodiments, a special bone block forming tool, also referenced as a bone block cutting guide, is provided to remove and shape a bone block from the tibial spine. The bone block forming tool may separate a portion of the tibial bone that includes the ACL insertion from other portions of the tibia. The bone block and attached ACL may be repositioned and/or otherwise moved aside to allow the surgeon free access to the tibia and/or femur to prepare the relevant bones to receive implant components. Once the femoral and/or tibial implant components have been implanted, the bone block and attached ACL can be reattached to the tibia (and/or attached to the tibial component, if desired and/or necessary) and/or could be repositioned in a notch or other feature of the tibial implant such that the ACL and attached bone block regain some or all of their function in stabilizing the knee. In various alternative embodiments, if the surgeon did not like how the ACL reconstruction turned out and wished to employ a standard total knee arthroscopy implant and associated surgical procedures, the bone block could be removed and the ACL transected, allowing for the insertion of the standard components.

In various embodiments, the implant components can include features such as cutout sections, notches or "windows" for accommodating various portions of the patient's natural anatomy, including bony anatomical structures and/or soft tissue structures. Desirably, a cutout can act as an anchoring site for the bone block and attached ACL and/or PCL after implant insertion. In various embodiments, cutouts can also facilitate the positioning and/or anchoring of a tibial implant prosthesis to the underlying anatomical structures. In addition, various embodiments of tools and procedures described herein facilitate the preparation of the patient's anatomical structures for the implant components.

In various embodiments, the inventions described herein include systems having ligament retaining components and associated surgical techniques, including tibial or femoral component systems, guides, tools and surgical techniques. The inventions described herein may be successfully applied to other damaged or diseased articulating joints, or opposing joint structures (i.e., creation of bone blocks and associated connective tissue anchoring locations on one or both opposing surfaces of a joint, such as the tibia and/or femur, where appropriate) including procedures where a surgeon desires to preserve natural ligaments and/or other underlying anatomical structures. Such joints can include various other joints of a body, e.g., ankle, foot, elbow, hand, wrist, shoulder, hip, spine or other joints. Also, various embodiments described herein can be successfully applied to total knee, bicompartmental or unicompartmental knee surgery.

In various embodiments described herein, the surgeon may use the surgical tools described herein to remove a section of bone with the ACL attached ("bone block"), and dislocate the bone block to facilitate the use of guide tools, jigs and/or surgical tools to expose and prepare surfaces of the tibia, which can be more easily accommodated and performed when the tibia has been subluxed relative to the femur. If desired, the various implants, tools, and procedures described herein facilitate the employment of ligament repair and/or replacement procedures, including the restoration of natural or artificial ACL and/or PCL structures, after the various joint replacement and/or resurfacing procedures described herein have been accomplished.

In various alternative embodiments, it may be desirous that the surgeon alternatively and/or additionally removes portions of the ACL from the femur, and in such cases an exemplary femoral implant, tibial implant, and/or surgical cutting tools could be provided that includes features for creating and reattaching a femoral or tibial bone block to the implant component in a manner similar to that described herein in connection with the tibia.

Disclosed herein are various advanced methods, devices, systems for implants, tools and techniques that facilitate the surgical repair of a knee joint while allowing retention, repair and/or replacement of the natural ligaments of the knee (and/or other related structures), thereby desirably preserving controlled rotation and translation of the repaired joint. In many embodiments, the procedures can provide adequate pain relief, preserve normal axial alignment of the limb, and preserve stability.

BRIEF DESCRIPTION OF THE SEVERAL VIEWS OF THE DRAWINGS

The foregoing and other objects, aspects, features, and advantages of embodiments will become more apparent and may be better understood by referring to the following description, taken in conjunction with the accompanying drawings, in which.

DETAILED DESCRIPTION OF THE INVENTION

Ligament Preservation

The various embodiments described herein may facilitate the retention of both the PCL and ACL, which can significantly impact the surgical procedure in a variety of ways. For example, where an ACL is sacrificed, damaged or is otherwise deemed unnecessary, the removal of such structure often improves the ability of the surgeon to access the tibial and/or femoral surfaces. When the ACL is severed or otherwise released, the tibia can be advanced some distance anterior relative to the femur, which allows the surgeon to dislocate the knee to some degree and gain better access to the upper surface of the tibia from a more cephalad orientation. In a similar manner, severing or release of the PCL can facilitate some degree of advancement of the femur relative to the tibia. In contrast, when the femur and tibia are retain its connection together via the flexible structures of the ACL and PCL, the healthy ACL and PCL cooperate to allow the femur to rotate relative to the tibia (in a known manner and relationship), the ligaments further cooperate to limit relative motion between the tibia and femur in an anterior/posterior direction for stability and alignment, and/or a surgeon's direct access to the upper surface of the tibia may be limited to the anterior face of the tibia with some limited access space between the articulating surfaces of the femur and tibia. As a result, it is advantageous to create implants, tools and techniques that may obtain the advantages of ligament retention and ligament release during the knee surgery.

Accordingly, various embodiments described herein facilitate the surgical repair and/or replacement of tibial and/or femoral articulating surfaces and associated structures via a less-invasive and/or minimally invasive approach. In addition, various embodiments described herein can be utilized with equal utility in open surgical procedures where the ACL and/or PCL have been retained (bicruciate bone blocks) as described herein.

Figure 1:
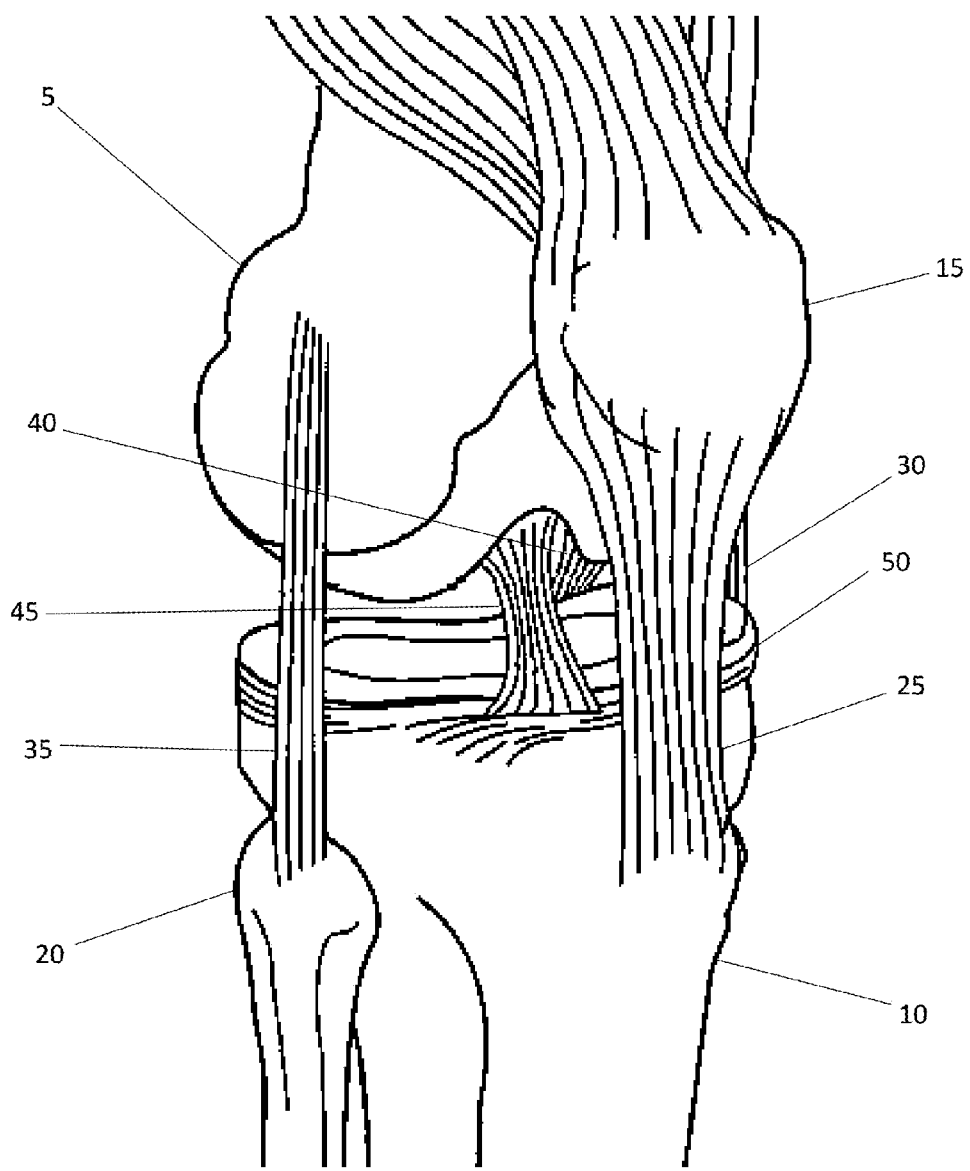
FIG. 1 depicts a perspective view of a knee joint, showing associated hard tissue structures and soft connective tissues.

FIG. 1 depicts a perspective view of a knee joint, showing a femur 5, a tibia 10, a patella 15 and a fibula 20. A number of connective structures extend between the various bones and/or other structures of the knee, including the patellar tendon 25, the medial collateral ligament 30 (MCL), the lateral collateral ligament 35 (LCL), the posterior cruciate ligament 40 (PCL) and the anterior cruciate ligament 45 (ACL). Also shown is the meniscus 50, which is depicted between the femur 5 and the tibia 10.

Figure 2:
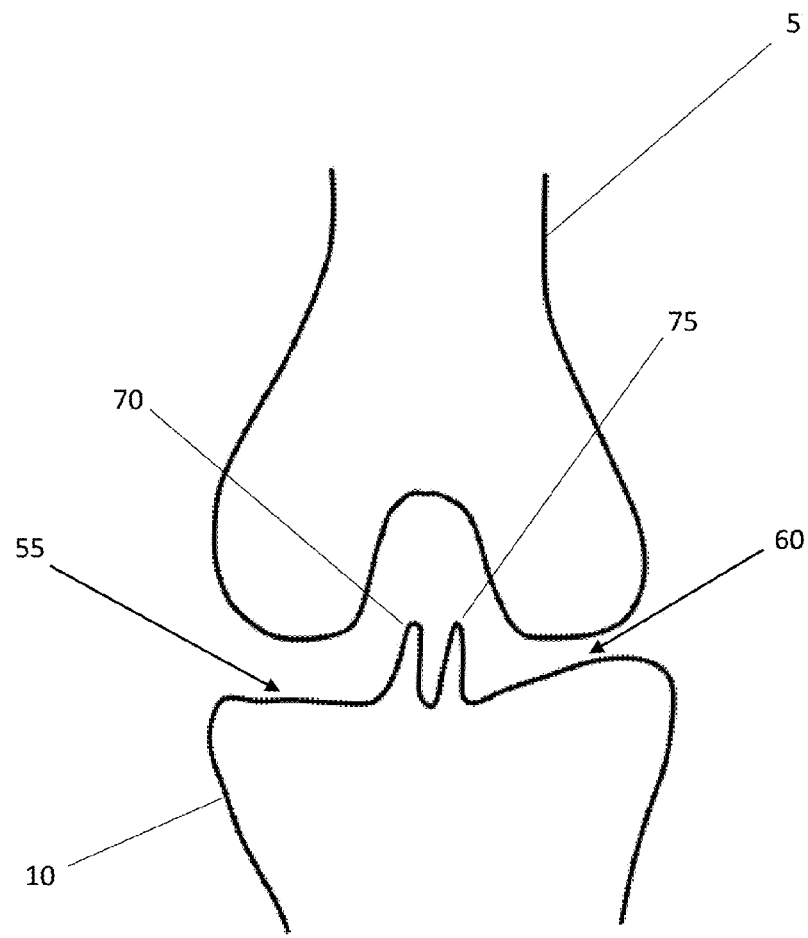
FIG. 2 depicts a frontal view of the femur and tibia bones of the knee joint of FIG. 1.

FIG. 2 depicts a frontal view of the femur 5 and tibia 10 of the knee joint of FIG. 1, the tibial surface including a medial surface 60, a lateral surface 55 and a central region 65 (not shown) which includes a medial intercondylar tubercle 75 and a lateral intercondylar tubercle 70.

Figure 3A:
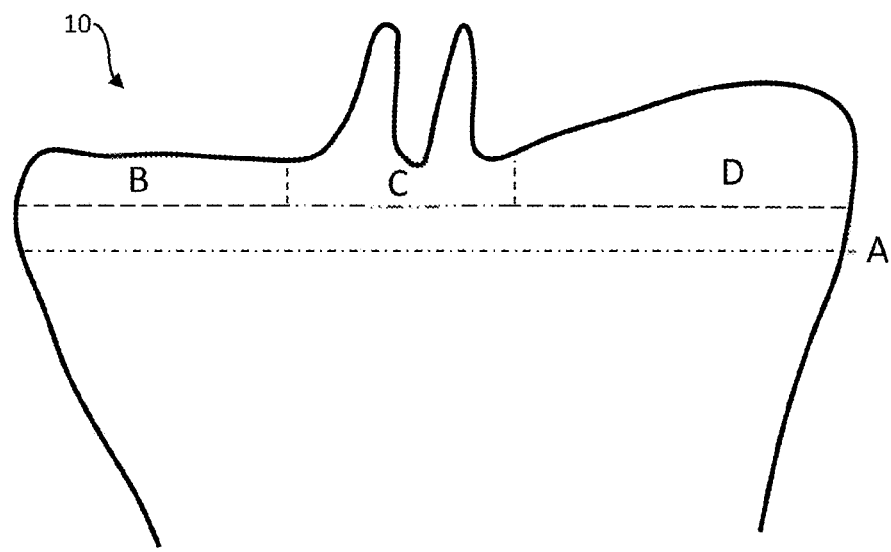
FIG. 3A depicts a frontal view of a tibia including a set of exemplary resection surfaces.
Figure 18:
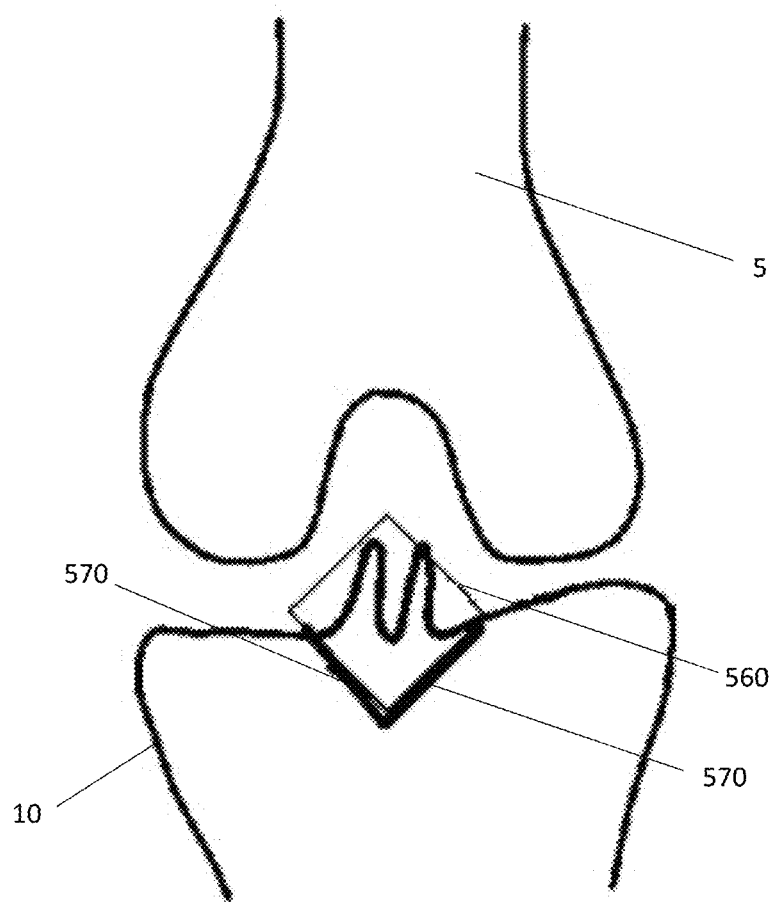
FIG. 18 depicts an embodiment of a wedge shaped bone forming tool and its corresponding cut to form a wedge shaped bone block.

FIG. 3A depicts a frontal view of a tibia 10 including a series of resection surfaces A, B, C and D. Traditionally, in a total knee joint replacement procedure a single planar resection of the entire tibia is performed, thereby creating a flat planar surface for placement of tibial components (not shown). Alternatively, a resection of one or more portions of the tibia (areas B and/or D) could be accomplished to accommodate unicoldylar and/or bicondylar replacement/resurfacing of individual articulating surfaces of the tibia. In various embodiments described herein, preparation of the tibial surface can include removal of material from multiple regions of the tibia, including B, D and some or all portions of C. If desired, the depth of the various tibial resections can be varied, and can include depths less than, equal to or greater than those shown (i.e., A, B, C and/or D) on the figure. In various embodiments, an upper portion of the surface of the tibia can be resected using any of the described bone cutting tools herein, where the anterior portion (section C) of the upper portion (which includes the insertion point of the ACL) may be separated from the remainder of the upper portion, a tibial implant is secured to the now exposed resected surface of the tibia, and the anterior portion including the insertion point of the ACL is returned and secured to the tibial implant and/or tibia, thereby restoring the function of the ACL to the surgically repaired knee. FIG. 18 shows an anterior-posterior view of exemplary resection cuts where one embodiment of a bone block may be cut and reattached to the tibia. (do we need an AP view showing tibial implant on top of cut surface of tibia with ACL bone block reattached to tibia?)

Figure 3B:
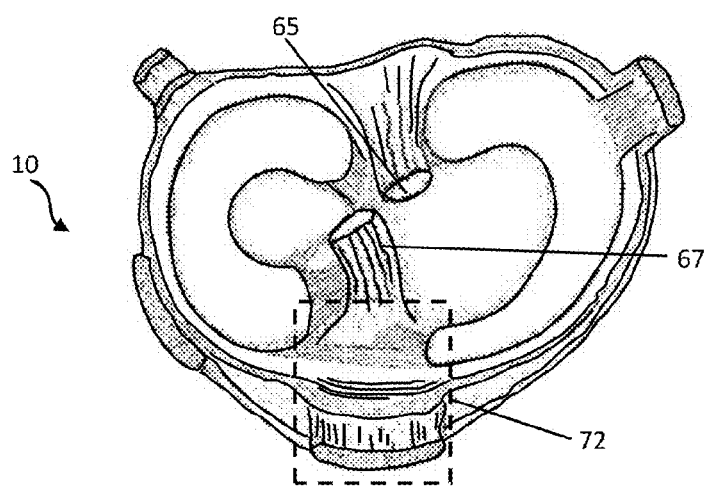
FIG. 3B depicts a top view of a tibia illustrating a common location of the ACL and PCL.

FIG. 3B depicts the top view of a tibia 10 illustrating the location of the ACL 67 and the PCL 65. In some embodiments, the surgeon may wish to preoperatively determine if the patient qualifies for this ligament preservation technique, verify the location of the ligaments, and/or assess the measurements of the ligaments and respective bone 72, and/or make surgical tool selections to make a final decision whether to preserve the ACL and/or PCL during the surgery. The surgeon may employ a series of preoperative images or scans during a patient's pre-operative range of motion, such as pre-operative flexion contracture, pre-operative extension lag, pre-operative ligament balancing, pre-operative ligament tension, and/or pre-operative coronal alignment, and then assess these results and compare them to the overall combined thickness of the intended prosthesis (femoral component, polyethylene component, and tibial component) to assist with the determination. Once the surgeon has made this determination, the surgeon may proceed to order, acquire or custom design the various tools and/or its components from the manufacturer that are necessary for surgery by analyzing the preoperative data. Alternatively, a minimally invasive procedure or other arthroscopic procedures on the patient's knee or other anatomical structure could be conducted to preoperatively determine whether the ACL and/or PCL is torn and/or sufficiently stable to proceed with preservation.

Bone Block Tools

In various embodiments of the present invention, a special bone block forming tool (also referenced as a bone block cutting guide—BBCG) can be provided to shape a bone block from the tibial spine. As seen in FIG. 3B, the ACL 67 may be positioned anteriorly and centered with one end of the ACL 67 attached to the tibial bone 10. Similarly, the PCL 65 may be positioned posteriorly and centered with one end attached to the tibial bone 10. Using preoperative images and data or other acceptable methods known in the art, the surgeon may select the proper bone block cutting guide to cut an optimal portion of bone from the proximal tibia 72, with the block remaining connected to the ACL 67. The bone block forming tool may be designed with a specific and/or a desired bone block shape that can accommodate a currently available tibial prosthesis design or a custom designed tibial prosthesis.

In various embodiments, the bone block may have a substantially rectangular shape, with a size that is approximately 5-10 millimeters wide, 5-10 mm thick, and 10-15 mm long. Of course, other shapes may be obtained, depending upon the shape of cutting tools (i.e., square, wedge, dove-tailed shaped, curved) and/or the surgeon's preference. The bone block size may also vary, depending upon the surgeon's preference or patient's anatomy. A patient specific bone block could be made to maximize the healing of the bone block back to the proximal tibia and minimize the chance of a bone block fracture or non-union (during and/or after surgery).

In various embodiments, the surgical tools (i.e. bone block forming tools or bone block cutting guides) for cutting the bone block may be formed in a fully integrated, one-piece design or could be modular with one or more pieces provided that assist the surgeon with placement, removal, and/or adaptation of the bone block guide and/or tools with other tools, jigs or instruments commonly used during knee surgery or other joint surgeries.

Figure 4A:
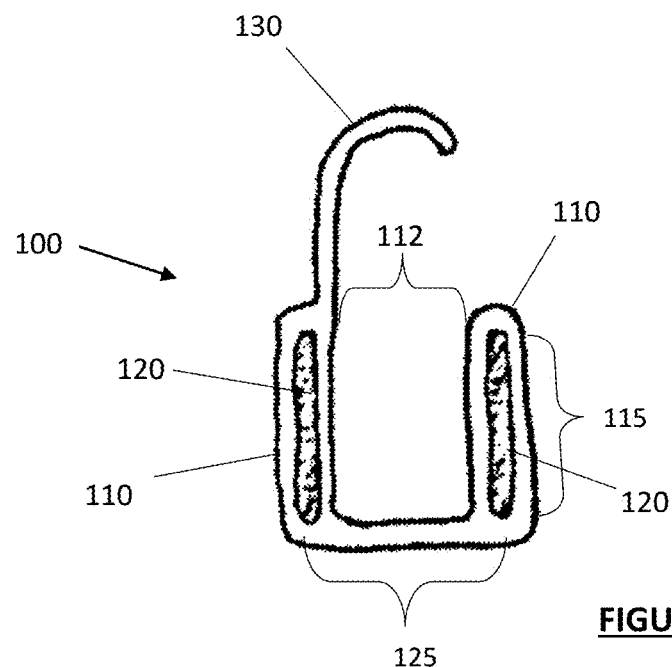
FIGS. 4A and 4B depict one exemplary embodiment of a bone block cutting guide.
Figure 4B:
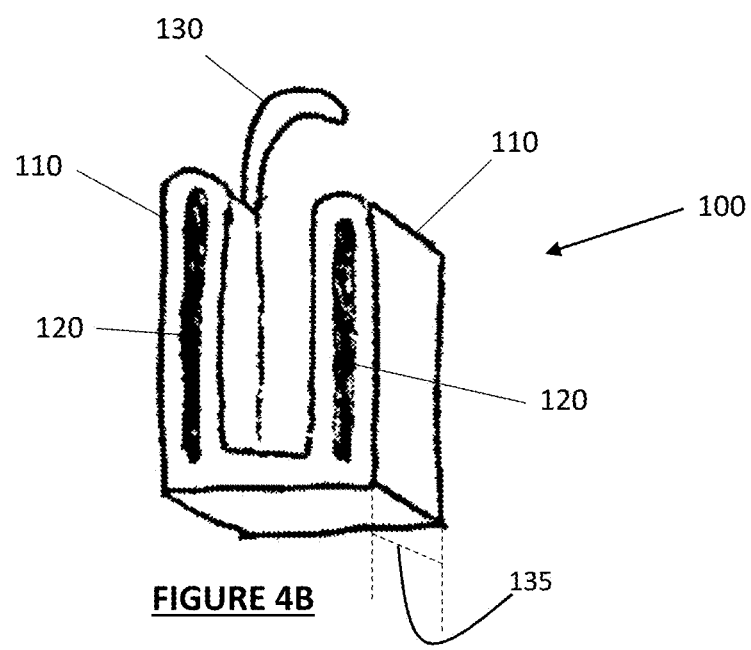

FIGS. 4A and 4B depict one embodiment of a bone block cutting guide 100 that can guide a reciprocating saw blade to make two sidewall cuts. The bone block cutting guide 100 includes at least two walls 110 and at least two slots 120 that can accommodate a blade of a reciprocating saw or similar surgical tools. The bone block cutting guide 100 may include a channel 112 that may be sized, matched, and/or conform to the dimensions of the ligament that will be preserved. The bone block cutting guide 100 may be designed with a small hook 130 or other feature that can be attached to the saw guides 110, where the hook is sized to fit the dimension of the ACL or appropriate ligament when the saw guide is in a desired position. The hook 130 may be placed in various positions on the bone block cutting guide. The hook 130 may be positioned in a similar plane of the slots 120 to allow for cutting the block on the articular tibial surface, the hook 130 may be placed in an offset plane of the slots 120 (as shown in FIG. 4B) or the hook 130 may be positioned in a perpendicular plane (not shown) of the slots 120 to allow for cutting the block on the anterior surface of the tibia. The hook may also be an integrated piece or a modular piece. In use, the hook 130 is placed around the ACL insertion on the tibia with the ACL approximately centered in the block and the block may be placed on the articular tibial surface (a non-resected surface), which desirably ensures that the ACL insertion point is centered prior to cutting or removing a portion of the tibial bone. The ACL may naturally lie in the channel 112 of the bone block cutting guide 100 during cutting. The surgeon may then use a simple osteotome and/or reciprocating saw to cut the posterior portion of the bone block. If desired, the surgeon may first make a standard horizontal proximal tibial bone cut (as shown in FIG. 3A, section A). A thin metal shim or plate could slide into this horizontal saw cut to protect the tibial plateau bone from the reciprocating saw blade as it cut down through the slot 120.

The slots 120 may be designed to determine the overall size of the desired bone block. The slots may be configured to a desired height 115, width 125 and depth 135. These dimensions may be obtained from preoperative images of the patients' anatomy, or the manufacturer may decide to use a database library to provide several standard sizes to manufacture the bone cutting guide 100. These slots could be parallel or converge to a point such that a horizontal cut would be unnecessary.

Figure 4C:
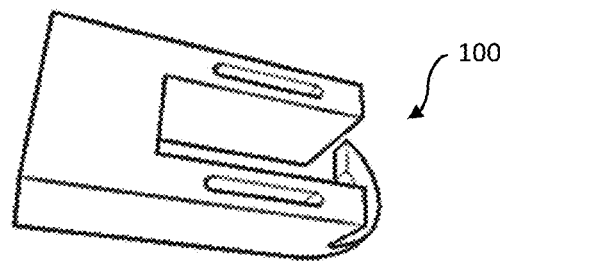
FIGS. 4C through 4E depict an alternative embodiment of the bone block cutting guide of FIG. 4A.
Figure 4D:
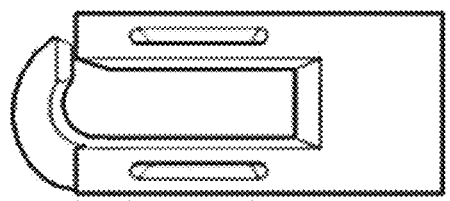
Figure 4E:
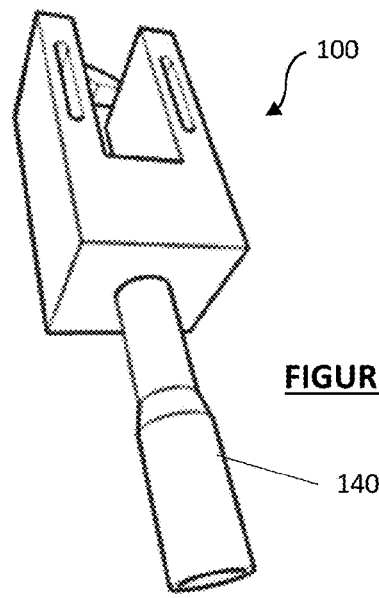

FIGS. 4C and 4D depict additional views of the bone cutting guide 100 of FIG. 4B. FIG. 4E depicts one alternative embodiment of the bone cutting guide with an associated handle 140. The handle may be integrated within the bone cutting guide 100 or the handle 140 may be modular for easy removal and attachment and/or storage in a surgical kit.

Figure 5A:
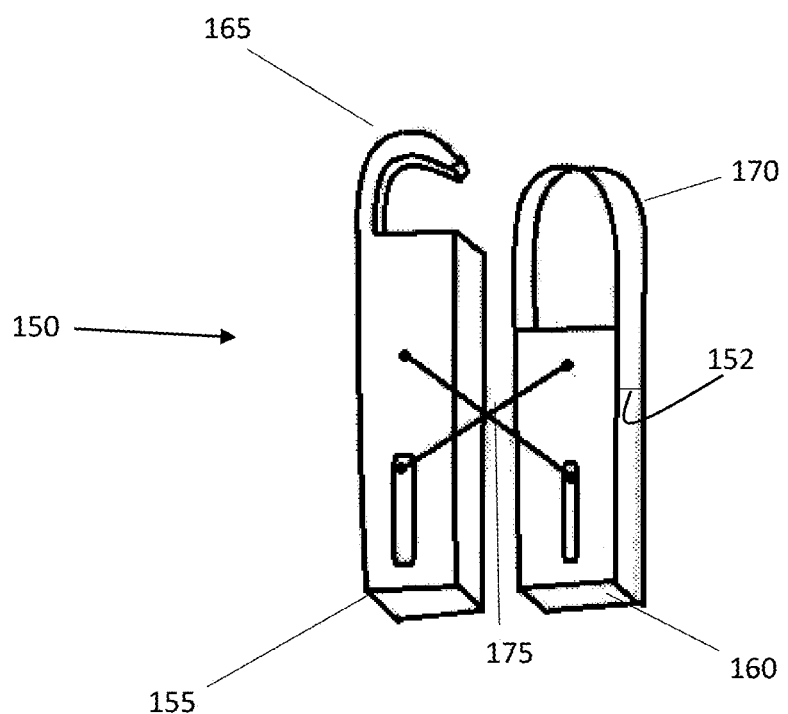
FIG. 5A depicts one alternative embodiment of a bone block cutting or forming tool.

FIG. 5A depicts one alternative embodiment of a bone block cutting guide 150 which includes an upper section 155 and a lower section 160. The upper section includes a hook 165 which sized to fit the dimension of an ACL when the bone block cutting guide 150 is in a desired position. The lower section 160 includes a rectangular box or cutter 170 having an edged or cutting surface on an upper edge, which can be formed in any shape, including a rounded, curved, wedged and/or rectangular block shape. The rectangular box or cutter 170 may have various sharpened surfaces, such as tapered blade edges, serrated edges, compound (double) bevels, chisels, chisel with back bevel, asymmetrical semi-convex, and/or any combination thereof. The rectangular box or cutter 170 may be modular or integrated within the lower section 160 of the bone block cutting guide 150. The upper and lower sections 155 and 160 are desirably connected by a compression connection or other arrangement, which in FIG. 5A is depicted as a 4-bar linkage 175. Alternatively, the compression connection may be any mechanism known in the art to allow or provide a compression connection between the two pieces. The upper and lower sections 155 and 160 desirably can be compressed together by the surgeon.

In use, the surgeon first would perform the standard proximal tibial bone cut at a depth that would allow for the implantation of the tibial components. The tibial bone from the articular side would be elevated from the non-articular tibial bone with a broad osteotome or similar instrument a great enough distance to allow the width 152 of the lower section 160 (see FIG. 5A) of the bone block cutting guide. The normal ACL attachment to the tibial spine (see section C in FIG. 3A) on the articular side of the tibial bone would be preserved through all these cuts. The tibial spine and the ACL attachment (see section C of FIG. 3A) would then be separated from the rest of the articular bone (the medial and lateral articular cartilage surfaces—see sections B and D from FIG. 3A) with the bone block cutting guide 150 (FIG. 5A). The lower section 160 of the bone block cutting guide will be inserted into the pre-cut section until at least a portion of the rectangular box or cutter 170 has reached the desired depth (i.e. cutting the bone block from underneath or inferiorly). The upper section 155 can be advanced over the planned area on the tibia to be cut, or the tibial cut section, with the hook placed around the ACL insertion on the tibia. The upper 155 and lower sections 160 can then be compressed together a desired amount to facilitate removal of the bone block. The upper section may also include a surface (not shown) that pushes down on the anterior portion of the bone block, if desired. Once the bone block is cut, it can be removed from the cutter 170 with the ACL still attached. In various embodiments, the side and anterior walls of the cutter 170 can cut the bone block such that the ACL insertion is centered in the block.

Figure 5B:
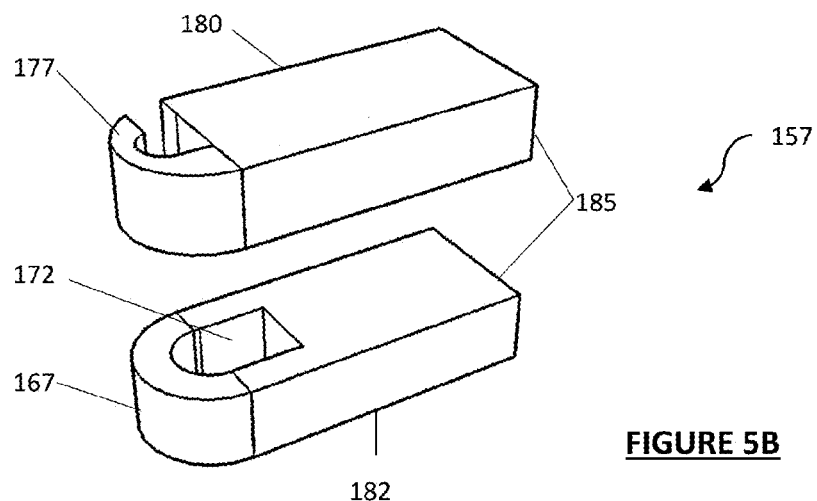
FIGS. 5B through 5D depict additional alternative embodiments of a bone cutting block.

FIG. 5B depicts an additional alternative embodiment of a two-piece bone cutting guide 157 of FIG. 5A, which may include integrated or modular components. The two-piece bone block cutting guide 157 may also include an upper portion 180 and a lower portion 182. The lower portion 182 may include a removable arch 167, where the surgeon may desirably remove the arch 167 and replace it with a different sized arch to allow more freedom cut a larger or smaller bone block size. The arch 167 may have various sharpened surfaces, such as tapered blade edges, serrated edges, compound (double) bevel, chisel, chisel with back bevel, asymmetrical semi-convex, and/or any combinations thereof.

The upper portion 180 of the two-piece bone block cutting guide 157 may include a hook 177 that will help the surgeon to center and/or displace the ACL while cutting the bone block. The upper portion 180 and the lower portion 182 may be designed with a compression connection as shown in FIG. 5A or FIG. 5B, securing or pinning mechanisms or any other mechanism known in the art. Furthermore, the back faces 185 of the upper portion 180 and the lower portion 182 may also be designed with a back plate 190 as shown in FIG. 5D. In various designs, a back plate 190 as shown in FIG. 5D may be provided that connects to the bone blocks 180 and 182 in a removable and slideable fashion, allowing the back faces 185 of the bone cutting block guides to slide along the back plate 190.

Figure 5C:
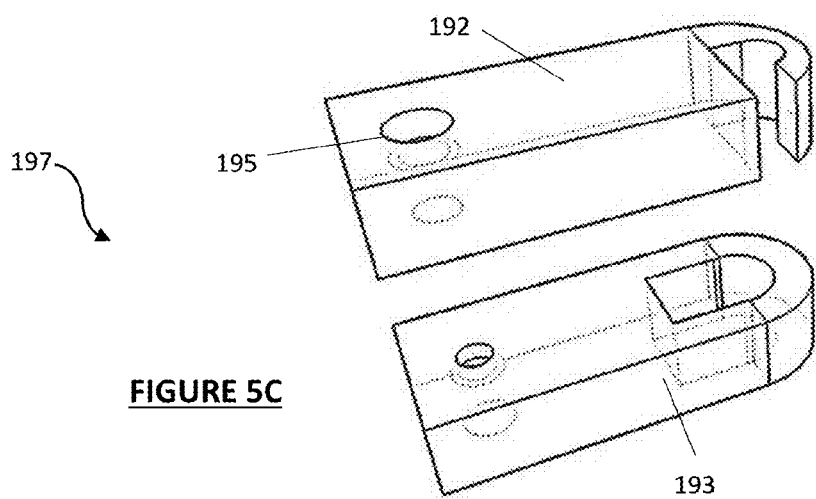
Figure 5D:
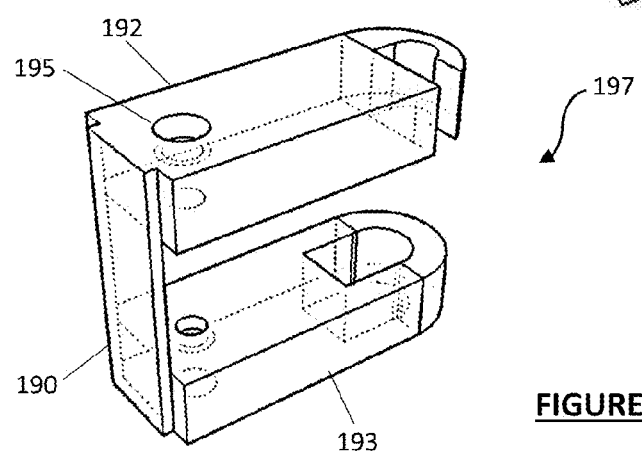

FIGS. 5C and 5D depict additional alternative embodiments of two-piece bone cutting guides 197 of FIG. 5A, which may include integrated or modular components, a compression member, pinning mechanisms, and/or removable or slideable back plate. The two-piece bone cutting block guides 197 may include a through-bore 195 where a screw type compression mechanism may be inserted. The through-bore 195 will be co-aligned with the upper portion 192 and the lower portion 193 to allow for a compression connection, where the upper 192 and lower 193 portions move toward each other to cut bone. Alternatively, the through-bore 195 may be designed to secure the upper 192 and/or lower 193 portions to any surface of the tibia (i.e. the anterior or articular surface) by using standard OR pins—thus, preventing linear or rotational movement.

The two-piece bone cutting block guides 197 may also be equipped with a slideable and/or removable back plate 190 (as shown in FIG. 5D), where the back plate 190 may allow linear translation while compressing the upper 192 and lower 193 portions of the bone cutting block guides. The back plate 190 may also serve as a positive stop on the anterior surface of the tibial bone, preventing the two-piece bone block cutting guide 197 from sliding posteriorly during cutting.

Although, the surgeon may use the two-piece bone block cutting guide 157 and 197 in a manner similar to that described in FIG. 5A, the surgeon may adapt the modular tool to a variety of different procedures. For example, the arch 167 on the lower portion 182 may also be used to trap the ACL. If desired, the surgeon may disconnect the arch 167 from the lower portion 182 to encircle or place the arch 167 around the ACL for protection, and reconnecting the arch 167 to the lower portion 182. Once the ACL is trapped, the surgeon may choose to use the upper portion 180 to center the ACL, and the surgeon may cut on the outside of the arch 167 to remove the bone block and prevent severing of the ligament. In addition, the removable arch 167 may produce an enclosure or restricted area 172 where the surgeon may insert an osteotome, reciprocating saw, or other similar surgical tools to cut a desired or predetermined bone block size.

Figure 6A:
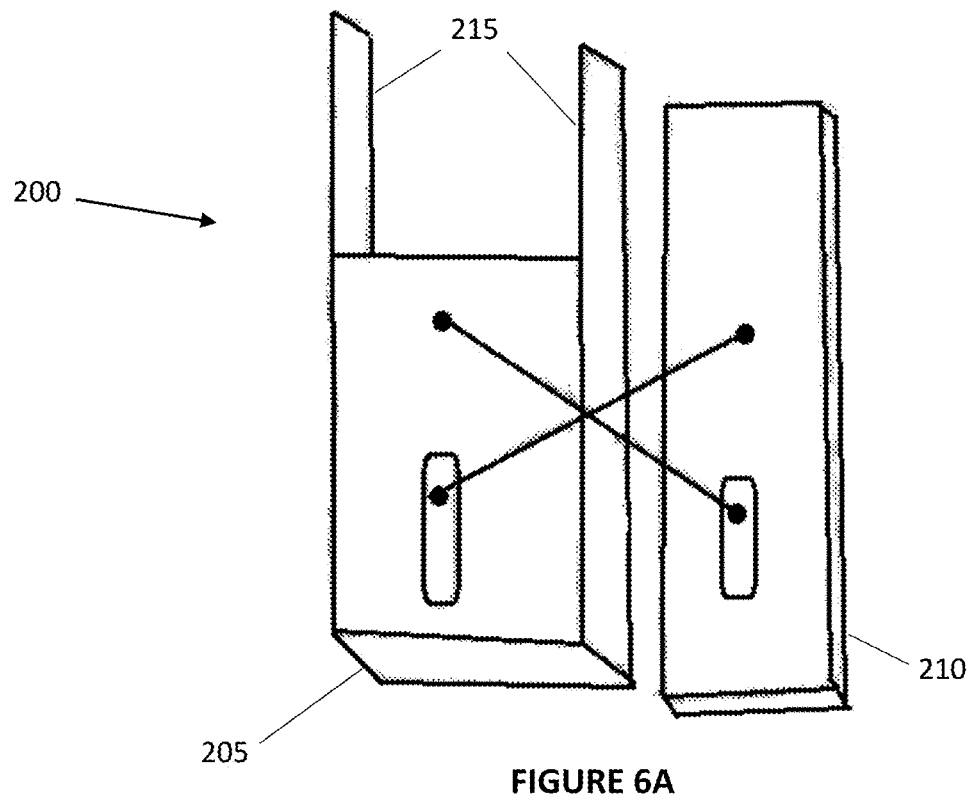
FIGS. 6A and 6B depicts alternative embodiments of a bone block forming tool.

FIG. 6A depicts an alternative embodiment of a bone block cutting guide 200, where the tool has a superior portion 205 that cuts down on the tibial bone and cuts at least two sides of the bone block. The superior and inferior portions are desirably connected by a compression connection, which in FIG. 6A is depicted as a 4-bar linkage. The inferior portion 210 of the tool can be a comparatively thinner metal shim that slides into a horizontal proximal tibia bone cut made by the surgeon. The inferior portion 210 may be used as a protective plate while the surgeon is conducting the bone cut or the plate is used as leverage to provide compressive force for cutting. The inferior portion 210 could slide into the standard horizontal cut (see section A in FIG. 3A) that surgeons make while removing the necessary tibial bone to make room for the tibial component. The superior portion 205 can have a similar hook or other feature (not shown) that can center the ACL insertion in the bone block. The superior portion also has a pair of vertical side walls 215 having an edged or sharpened lower surface for cutting the tibial bone as the tool 200 is advanced into the bone. The side walls 215 may be designed with a variety of sharpened surfaces, such as tapered blade edges, serrated edges, compound (double) bevel, chisel, chisel with back bevel, asymmetrical semi-convex, and/or any combinations thereof.

In this embodiment, the inferior portion 210 could be slid or inserted into a previous lateral bone cut in the tibia made by the surgeon using commonly available saws until the surgeon reaches the desired depth. The superior portion 205 with the sidewalls 215 may desirably straddle the ACL insertion point. The surgeon may subsequently apply compression between the superior 205 and inferior 210 portions to cut a bone block out of the tibial bone portion.

Figure 6B:
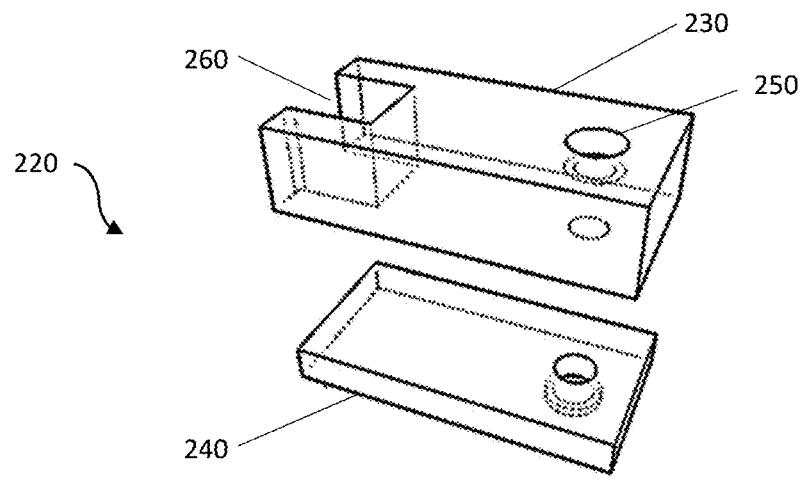

FIG. 6B depicts an additional alternative embodiment of the bone block cut guide of FIG. 6A. In this embodiment, the two-piece bone block cut guide 220 may have a superior 230 and inferior portion 240, a thread-screw compression connection mechanism or a pinning mechanism inserted in the bore 250, and/or a guide aperture 260. A thread-screw compression connection mechanism may be inserted in the bore 250 to allow the surgeon to fix, secure and/or stabilize the inferior 240 and superior 230 portions by compressing the pieces toward each other to cut a bone block. The thread-screw compression connection mechanism may also be used as a positive stop to prevent posterior advancement during cutting of the bone block. The bore 250 may also be designed to allow standard OR pins to be placed to prevent movement or rotation. Furthermore, the guide aperture 260 may also be used separately to cut to a surgeon's desired size bone block. The surgeon may use a standard surgical saw and insert within the guide aperture 260 to cut the bone block.

Figure 7A:
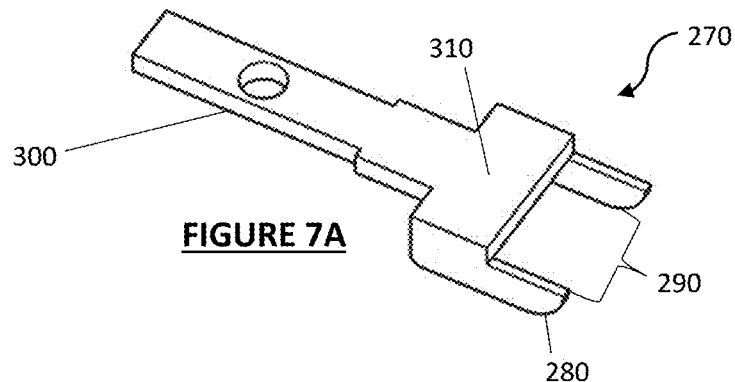
FIG. 7A depicts an additional alternative embodiment of a square-shaped bone block forming tool.

FIG. 7A shows a one-piece alternative embodiment of a bone block cutting guide 270. The bone block cutting guide 270 may come equipped with cutting surfaces 280 and an impacting surface 310. The cutting surfaces 280 may include a variety of blade shapes, such as tapered blade edges, serrated edges, compound (double) bevel, chisel, chisel with back bevel, asymmetrical semi-convex, and/or any combination thereof. The impacting surface 310 may be used by the surgeon when the surgeon places the bone block cutting guide 270 on the articular surface of the tibia or the anterior surface of the tibia, and the surgeon can subsequently impact the impact surface 310 with standard available impacting tools until the surgeon obtains the desired bone block size. The impact surface 310 may be available in alternative shapes, such as curved, radiused, and/or concave (not shown) to allow the ACL to fit or match within the shaped impact surface. The bone block cutting guide 270 may be designed with a variety of bone block widths 290, heights and/or depths. The sizes may be provided within a surgical kit should the surgeon require increased or decreased bone block sizes.

Figure 7B:
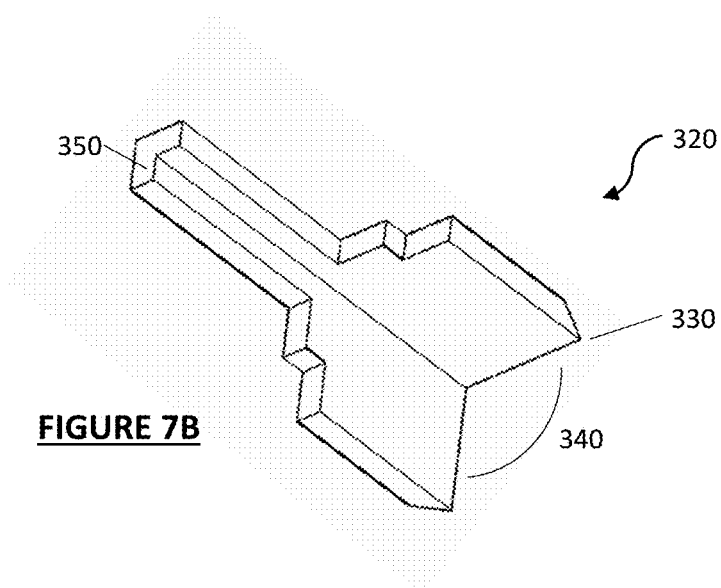
FIGS. 7B and 7C depicts additional alternative embodiments of a wedged-shaped bone block forming tool.
Figure 7C:
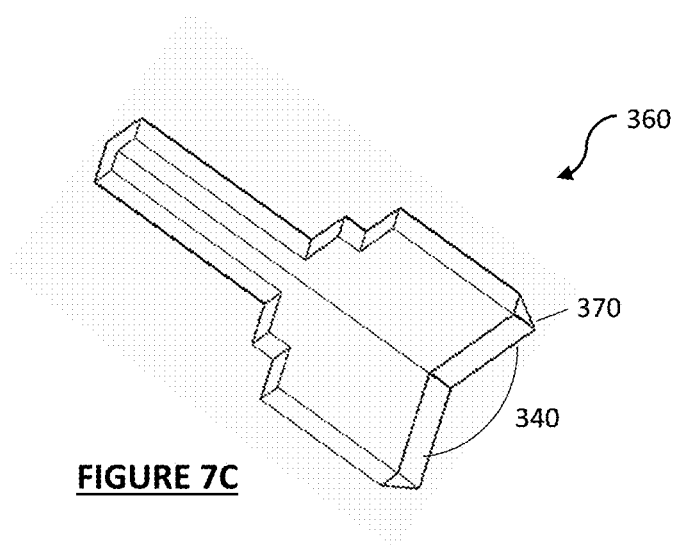

FIGS. 7B and 7C depict exemplary embodiments of a one-piece wedge-shaped bone block cutting guide 320 and a modular wedge-shaped bone block cutting guide 360. The wedge-shaped bone block cutting guides 320 and 360 may be impacted on the handle impact surface 350 while placed on the anterior surface of the tibial bone until the surgeon reaches the desired depth of the bone block. The surgeon may subsequently use a standard osteotomy saw to cut the remaining block from the tibia. The wedge-shaped bone block cutting guides 320 and 360 may be designed to accommodate various wedge shapes 340 (see FIG. 18) derived from dimensions predetermined from preoperative images or from a standard library database. Furthermore, the cutting surfaces 330 may be designed with a variety of sharpened surfaces, or modular cutting surfaces 370.

Figure 19:
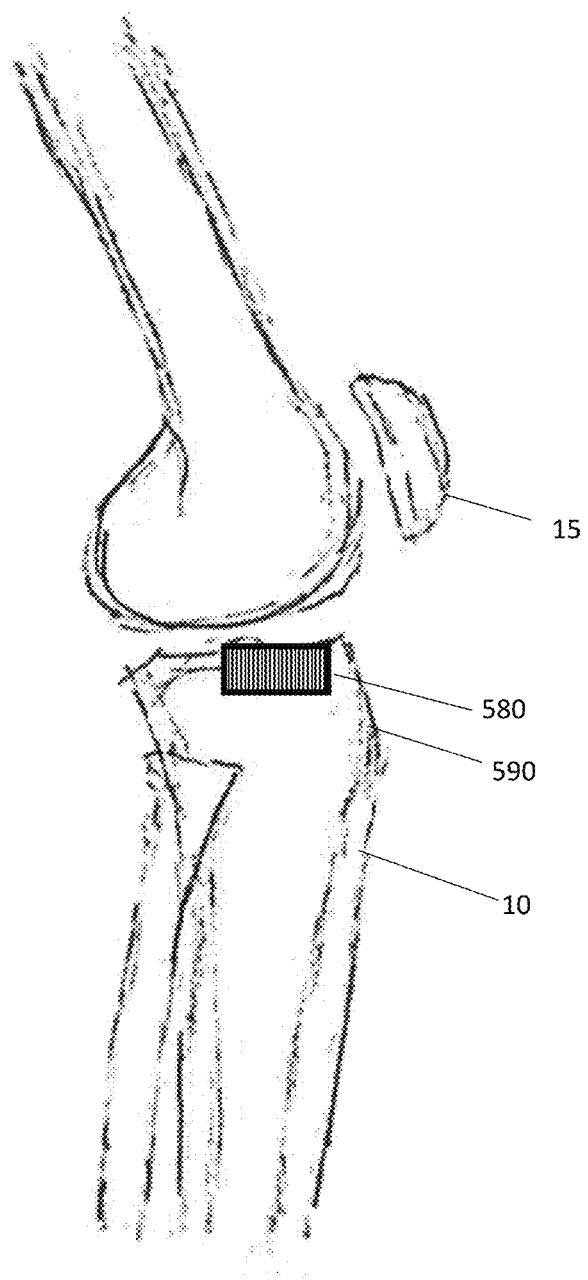
FIG. 19 depicts a lateral view of one embodiment of a bone block reattached to the tibia.

In an alternate embodiment, a bone block cutting guide may be designed to provide a cut area that is recessed or inset 580 from the surface of the tibia 10 as shown in FIG. 19. The surgeon may desirably cut the bone block away from the anterior surface 590 of the tibia for a variety of reasons and/or purposes, such as adjustment, correction, supplemental fixation and/or to accommodate bone degradation.

In another embodiment, a bone block cutting guide may be designed to reduce and/or eliminate the potential to violate the anterior tibial cortex while cutting the bone block (not shown). The bone block could be fashioned by two converging bone cuts, representing a wedge bone block 560. One cut could start at the medial articular surface of the tibia and head inferiorly and laterally. The other cut could start at the lateral articular surface of the tibia and head inferiorly and/or medially 570 (see FIG. 18). The two cuts would intersect approximately 1 cm below the articular surface. Anterior and posterior wall cuts could be made. The cuts could be made with an osteotome, a reciprocating saw, or any other readily available cutting tool in the OR. The bone block forming tool may be designed as a patient specific guide or jig to help guide all 4 cuts made to the tibia.

In an alternative embodiment, the bone block cutting guide could be a 3-sided punch (inferior bone cut and 2 side walls) (not shown) that is advanced from the anterior cortex of the tibia in a posterior direction. The 3-sided punch could also guide a reciprocating saw blade. The punch could be inserted into the tibial bone a set distance. The posterior wall cut could be made with an osteotome. The 3-sided punch could be guided into the correct position by a patient specific tibial jig. The same tibial jig could also guide the proximal tibial bone cut after the bone block was fashioned and mobilized out of the tibia.

In various embodiments, the bone block cutting guide tools may be designed to be integrated with various commercially available tibial and femoral resection blocks, templates or cutting guides for further support, securement, alignment, etc. In other various embodiments, the bone forming tool may be designed as adjustable to accommodate or adapt the tool to a desired thickness of a specified bone block, or to a desired plane to cut the bone block. For example, if the overall thickness of the bone block was too thin to get adequate healing of the bone block back to the proximal tibia or risked the possibility of the a bone block fracture, then the bone block could be fashioned such that the bone block was substantially bigger than it otherwise would have been if the horizontal tibial cut was made first. Any embodiment of the tool can be made adjustable, and it could fashion the bone block out of the proximal tibial bone before the horizontal tibial cut is made. The horizontal or inferior bone cut for the bone block could be made below the intended horizontal bone cut for the tibial implant. The bone block could be a thicker piece of bone in the cephalad to caudal direction than the articular bone thickness that is removed with the horizontal tibial cut. The floor of the bone block could be below the cut surface of the proximal tibia so that the bone block would be substantially thicker.

The bone block could be bi-cortical (not shown). The position of the intended bone block could be verified first with a guide wire that could be inserted from the ACL insertion on the tibia and directed towards the anterior tibial cortex. Alternatively, the guide wire could be started on the anterior tibial cortex and directed toward the ACL insertion with a guide that is well known in the art. The surgeon could then slide a cylindrical reamer over the guide wire and drill a cylindrical core of bone that would include the ACL attachment on one end. The same guide wire and cylindrical reamer could also be used on the femoral side as well to remove the ACL insertion from the femur instead of from the tibia. The cylindrical bone portions from the tibia and/or femur with ACL attachment could be maneuvered into the knee joint (i.e. posteromedial, posterolateral, medially, laterally, and/or posteriorly) and out of the way. The implants could be inserted and then the cylindrical bone with ACL attachment could be repositioned back into the cylindrical hole from which it came. An interference screw or other attachment mechanisms could fixate the cylindrical bone block back to the native tibial or femoral bone.

The bone block could be fashioned to include both the ACL and PCL attachment on the same bone block (not shown). This bicruciate bone block could include both the anterior and posterior cortex of the intercondylar tibial region as shown in FIG. 18. The tibial prosthesis could then have a central opening or window to allow for reattachment of the bi-cruciate bone block. The tibial prosthesis might have a more robust post and keel to compensate for the structural weakness in the middle of the tibial component.

Tibial Prosthesis Embodiments

Figure 8A:
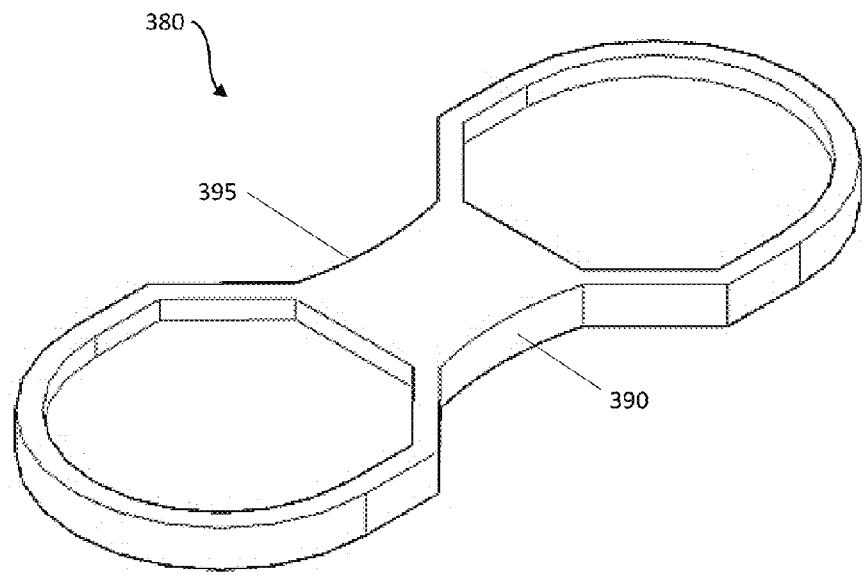
FIGS. 8A and 8B depicts one exemplary embodiment of a tibial prosthesis.

FIG. 8A depicts an isometric view one exemplary embodiment of a tibial prosthesis 380 for use with various embodiments previously described. The tibial prosthesis 380 may include an anterior cut-out section 390 and/or a posterior cut-out section 395 that desirably facilitates the reattachment of the bone block and ACL and/or PCL insertion (not shown) to the proximal tibia. In one embodiment, the anterior cut-out 390 may be designed to closely match, substantially match, or conform to the desired bone block dimensions. Alternatively, the anterior cut-out 390 may be designed completely open, which may allow the surgeon significant flexibility in placement and/or orientation of the bone block after implantation of the tibial implant has been achieved.

For example, the open anterior cut-out 390 described herein could be particularly useful where the ACL may require adjustment, such as changes in joint line height, coronal alignment correction, and ACL lengthening or shortening than an ACL preserving TKA by repositioning or modifying the bone block. If the ACL were too tight, then additional bone could be resected from the posterior side of the bone block to effectively allow the bone block to sit more posterior on the tibia and loosen up the ACL. Conversely, if the ACL were too loose, additional bone, polyethylene or some sort of spacer could be removed or placed behind, on the sides, bottom and/or at an offset dimension relative to the bone block to effectively move the bone block forward or any relevant direction to tighten the ACL graft. In various embodiments, if the bone block were cut asymmetrically, the rotation of the block to different orientations relative to the knee could potentially adjust the looseness and/or tightness of the ACL in a desired manner. Additional bone could be removed from the bone block to lower the block and tighten up the ACL graft. In various embodiments, the reattachment of the bone block to the tibia may result in different positioning, angulation, and/or orientation of the soft tissue attachment point relative to the preoperative positioning, angulation, and/or orientation (i.e. the different position may be medial, lateral, inferior, superior, anterior, posterior, angled, and any combination thereof relative to the preoperative position).

Figure 8B:
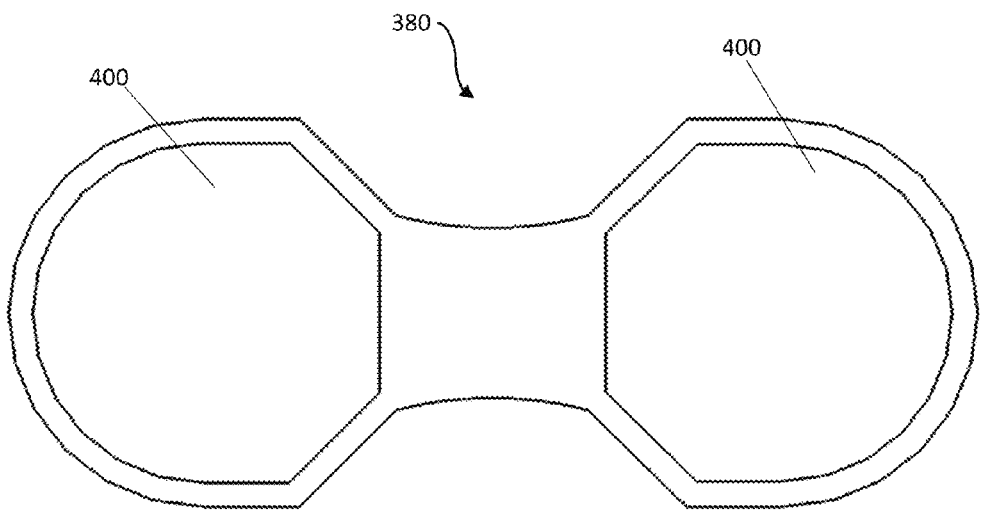

FIG. 8B depicts the top view of an exemplary embodiment of the tibial prosthesis 380 of FIG. 8A. The tibial prosthesis 380 may include recessed surfaces or trays 400 where tibial inserts (not shown) may be placed. In various embodiments, a tibial prosthesis 380 could also incorporate one or more locking mechanisms (not shown) to secure a polyethylene or other tibial insert into a tibial tray. In one exemplary locking mechanism, a corresponding lower surface on the tibial insert could engage one or more ridges on the surface 400 of the tibial tray, thereby locking the tibial insert in a desired position relative to the tray.

The tibial prosthesis 380 and the tibial inserts may be designed in a variety of sizes to accommodate patient knee anatomy. In some embodiments, the polyethylene is a one-piece polyethylene (as with most traditional total knee replacements). In some embodiments, the polyethylene is a two-piece polyethylene with a separate medial and lateral polyethylene. Various embodiments of the tibial implant could still include a central stem and/or keel.

Figure 9:
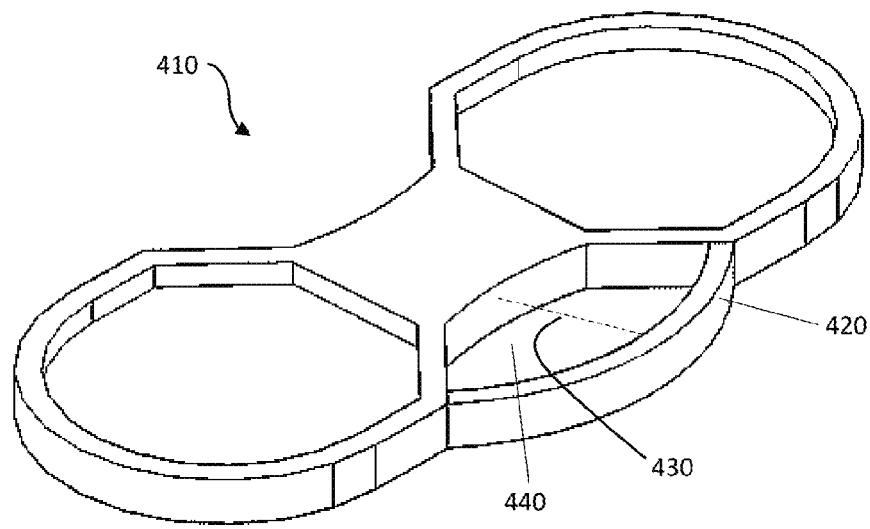
FIGS. 9 and 10 depict alternative embodiments of a tibial prosthesis.
Figure 10:
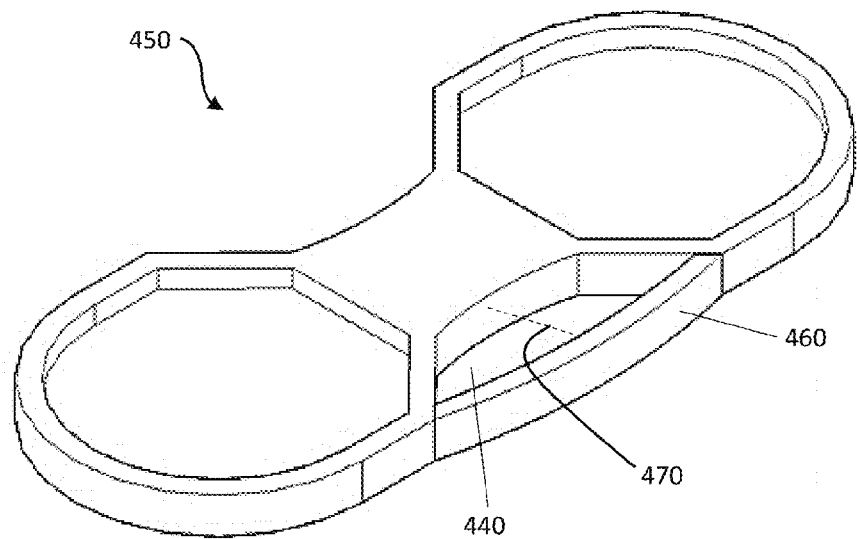

In other alternative embodiments, shown in FIGS. 9 and 10, a tibial prosthesis 410 and 450 could include a partially-blocked section with an anterior metal wall 420 and 460 or other feature on the partially-blocked section, which in this embodiment resembles a hole or restricted opening 440 in the tibial prosthesis. The anterior metal wall 420 and 460 may be designed with a variety of shapes and dimensions to substantially match or conform to the shape of the cut bone block. In one embodiment, the anterior metal wall 420 may be designed as an integrated one-piece design or as a two-piece design with releasable connection mechanisms or features. The anterior metal wall 420 may include or be replaced with a large radius 430 anterior metal wall to accommodate over-sized cut bone blocks to fit within the over-sized restricted opening 440. However, in one embodiment, the restricted opening 440 may be designed to closely match, substantially match, or conform to the desired bone block dimensions.

FIG. 10 depicts a tibial prosthesis 450 with a smaller restricted opening 440, where the anterior metal wall 460 may have a smaller radius 470 design to accommodate tighter or smaller cut bone blocks to fit within the restricted opening 440. In one embodiment, the restricted opening 440 may be designed with enough space to allow the surgeon significant flexibility in placement, orientation and/or modification of the bone block after implantation of the tibial implant has been achieved to correct varus/valgus alignment, ligament tightness/looseness, and/or other anatomical deficiencies. However, in other embodiments, the restricted opening 440 may be designed to closely match, substantially match, or conform to the desired bone block dimensions. Desirably, the anterior metal wall 430 and 460 may be available in different shapes and sizes that could be provided in a kit for the surgeon's convenience.

Figure 11A:
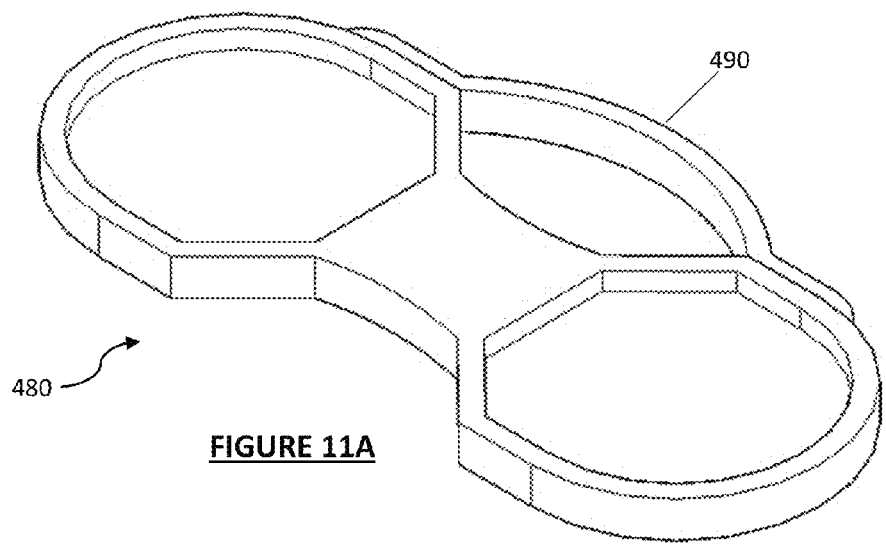
FIGS. 11A and 11B depict another alternative embodiment of a tibial prosthesis.
Figure 11B:
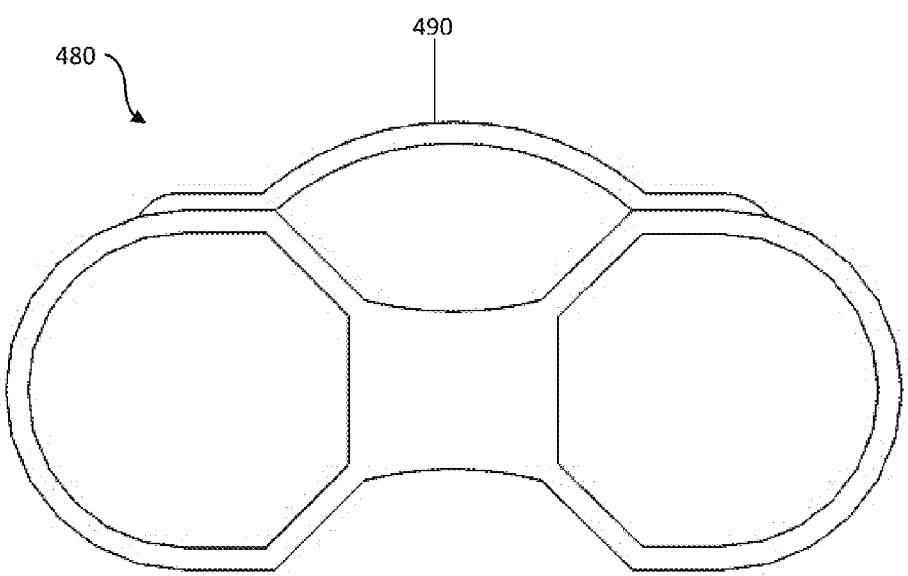

FIGS. 11A and 11B depict another alternative embodiment in various views of a tibial prosthesis 480 that includes a modular anterior metal wall 490 that may be connected to the outside of the tibial prosthesis 480. The modular anterior metal wall 490 could be releasably connected to the outer wall of the tibial prosthesis 480 using a variety of connection mechanisms known in the art. The modular anterior metal wall 490 may be designed to substantially match the thickness of the tibial prosthesis 490, or at least a portion of the modular anterior wall 490 may extend onto the anterior surface of the tibia for securing the bone block in place.

Figure 12A:
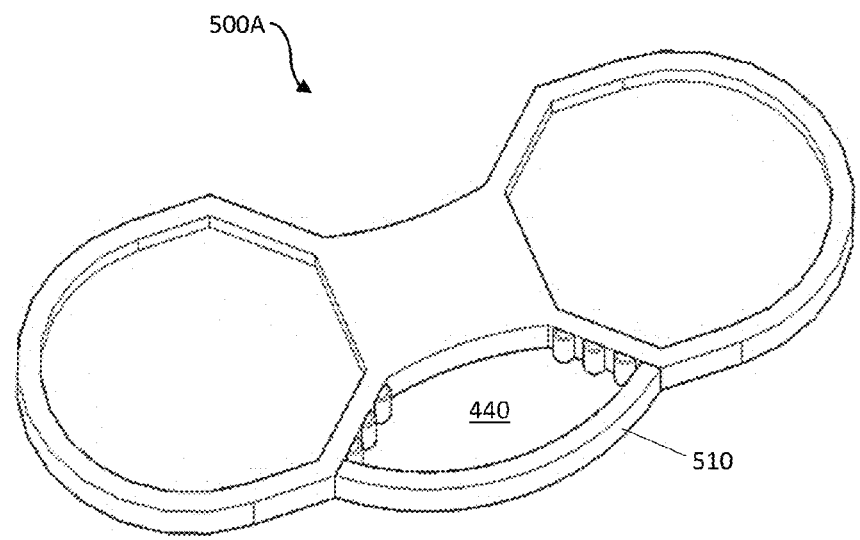
FIGS. 12A and 12B depicts exemplary embodiments of a tibial prosthesis that may have medial/lateral integrated features to allow securing of the bone block with a plurality of sutures.
Figure 12B:
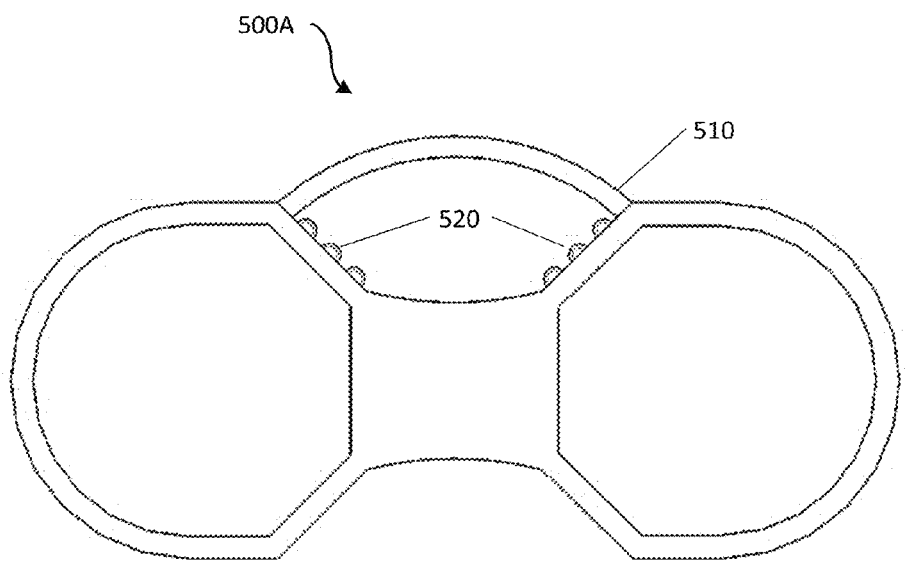
Figure 14A:
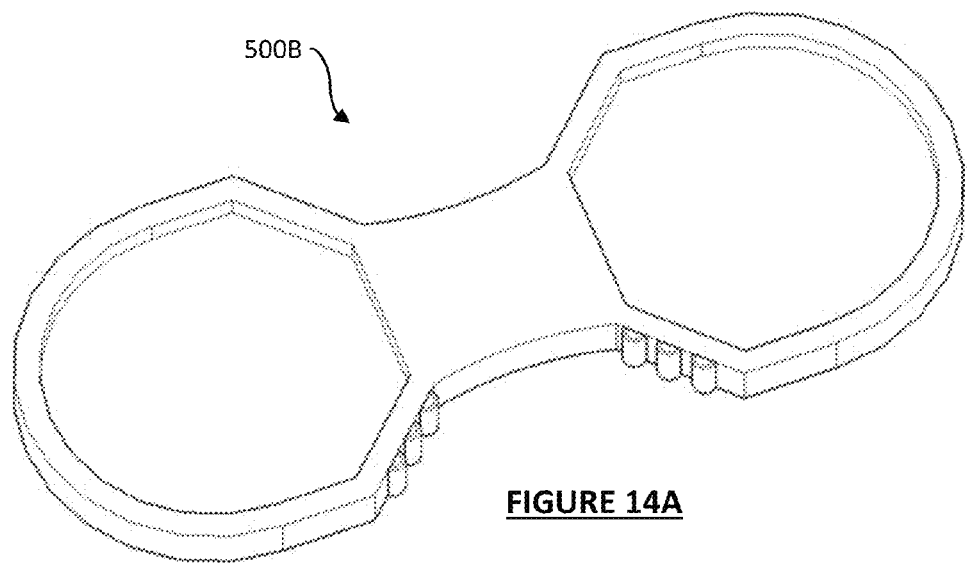
FIGS. 14A and 14B depicts exemplary embodiments of a tibial prosthesis that may have medial/lateral integrated features to allow securing of the bone block with a plurality of sutures and securing arm.
Figure 14B:
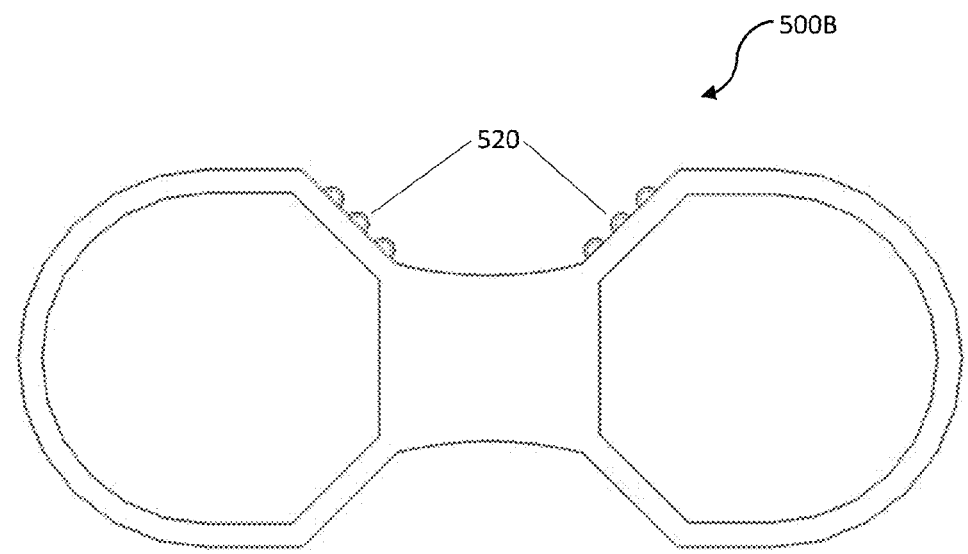

FIGS. 12A and 12B depict an alternative embodiment of a tibial prosthesis 500A that includes an anterior metal wall 510 and medial and/or lateral loops 520. In this embodiment, the tibial prosthesis 500A could include a plurality of loops or holes (not shown) in the medial and lateral side walls of the tibial prosthesis where the bone block would be positioned within the restricted opening 440. The loops 520 may desirably allow suture fixation over the bone block for further or additional securement, provide a tightening feature, and/or provide fixation to the tibial prosthesis 500A. Alternatively, the tibial prosthesis 500B may be used without the anterior metal wall 510, but retain the medial/lateral loops 520 for additional fixation of the bone block as shown in FIGS. 14A and 14B.

Figure 13A:
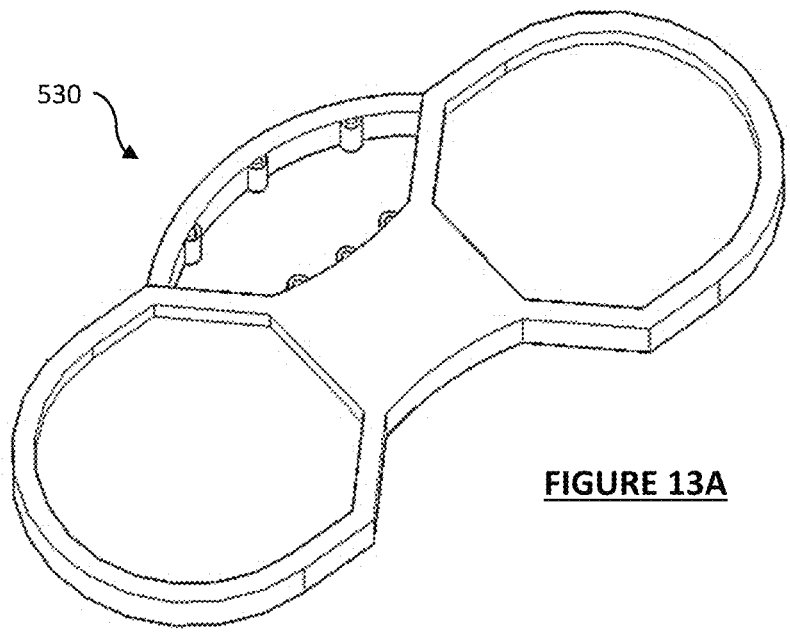
FIGS. 13A and 13B depicts exemplary embodiments of a tibial prosthesis that may have anterior/posterior integrated features to allow securing of the bone block with a plurality of sutures.
Figure 13B:
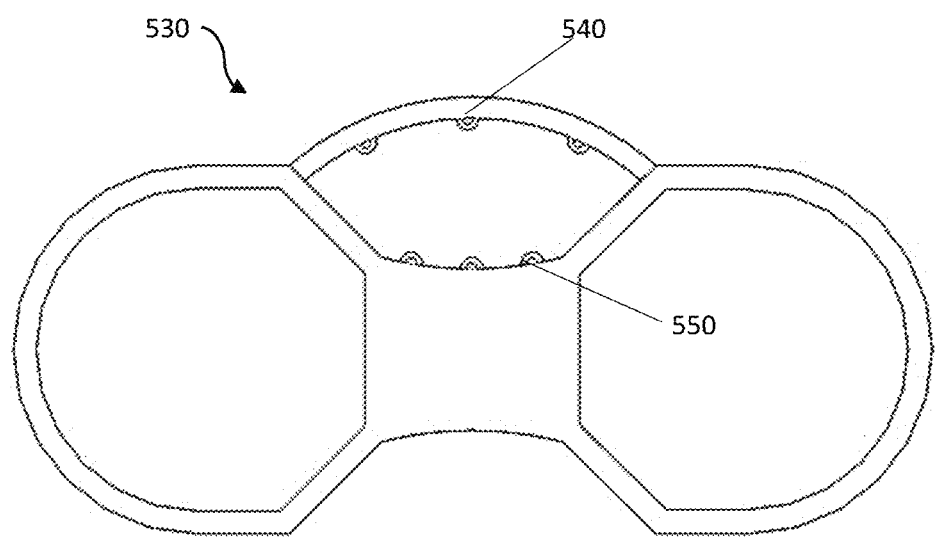

Similar loops could be provided in the anterior and posterior section of a portion of the tibial prosthesis 530, as shown in FIGS. 13A and 13B. The loops may be designed on the anterior metal wall 540 and/or the posterior/anterior wall 550 of the tibial prosthesis 530 of FIG. 13B, if desired. Alternatively, the loops may be placed on medial, lateral, anterior, posterior sides of the tibial prosthesis 530 or the anterior metal wall 540, and/or any combination thereof.

In another alternative embodiment of the tibial prosthesis, the tibial prosthesis could be designed to allow fixation of the bone block to the proximal tibia, anterior surface of the tibia, and/or tibial prosthesis using non-suture fixation (e.g., using a dove tail, polyethylene overhanging the bone block, screw fixation of the bone block into the proximal tibial bone, screw fixation of the bone block into the tibial component, belts and/or support rails around the block, etc.—not shown). A wide variety of other fixation modalities could be used to secure the bone block to the resected tibial surface, to the tibial component, and/or to various combinations thereof. In one exemplary embodiment, the bone block could be cut into an asymmetrical or other shape, such that the block could be rotated to a first direction for insertion through the anterior cutout, but subsequent rotation or manipulation of the bone block could wedge the bone block within the cutout and prevent egress (i.e., the bone block becomes too big to travel through the cutout in the second orientation).

Ligament Preservation Method

One significant feature of the various embodiments described herein is that the proposed surgical procedure does not require that a surgeon learn a completely new procedure or become familiar with a completely new set of implants and surgical tools to accomplish the surgical corrections described herein. The procedure allows the surgeon to resect the standard portion of the proximal tibia while retaining the ACL insertion on the tibia. This standard portion of the proximal tibia is resected regardless of whether the surgeon desires to preserve the ACL insertion. In addition, the design changes to the tibial tray so as to accommodate the bone block will not significantly alter the surgical procedure, nor will they significantly affect the strength and/or survival of the implant. The disclosed procedure also allows the surgeon the ability to sublux the tibia forward to improve exposure, which is typically performed with most knee replacements.

With the various improved devices and techniques described herein, a surgeon could preserve the ACL and PCL while performing a standard or modified improved total knee arthroplasty. The surgeon will be able to refrain from cutting the ACL insertion on the proximal tibia or damaging the ACL insertion on the tibia in any way. After making the horizontal, proximal tibial cut with any of the proximal tibial cutting guides that are readily used and known in the art, the surgeon can employ the various systems and embodiments described herein to create a bone block with the ACL and/or PCL insertion, include the use of any of the embodiments of bone-cutting and/or shaping tools contemplated herein.

The tibial bone block with the preserved ACL can be removed or separated from the rest of the proximal tibial bone, and moved out of the way to facilitate surgical access to the intended treatment site. Alternatively, the bone block cutting tools could be used to hold the bone block, and such tools may be designed with clips, clamps or other features that will assist the surgeon in setting the bone block aside during surgery. By moving the mobile ACL bone block out of the way, the surgeon is able to distract or otherwise manipulate the tibia and femur in a typical manner to allow the surgeon access to the entire tibial plateau and also the posterior knee structures. By moving the mobile ACL bone block out of the way, the surgeon can implant the tibial prosthesis perpendicular to the mechanical axis of the tibia.

For example, once separated from the tibia the mobile ACL bone block portion can be moved into the posterior aspect of the knee while the surgeon prepares the bone cuts on the distal femur and proximal tibia. Because the ACL and associated bone block can be treated similarly to a resected ACL, the preparation of the tibia and femur can be performed under protocols and methods well known in the art. Similarly, the tibial and femoral components can be secured into place through techniques and procedures used and well known in the art (e.g., cement or press fit).

After the proximal tibia and distal femur have been prepared or resected for their implant components, the ACL bone block can be reinserted into the precut area on the tibia and/or attached to the tibial implant. The bone block may be inserted before, after and/or concurrently with the various implant components, depending upon surgeon preference. The bone block may be manipulated, modified, repositioned, wedged, press-fit and/or otherwise mechanically secured into the original anterior cut out of the tibial component, if desired. The various mechanical securements may include alternative mechanical components or mechanical features carved into the bone block. For example, an interference screw could be wedged between the bone block and the tibial bone to secure the bone block to the tibial bone. The interference screw is a screw that may be indicated for fixation of soft tissue and bone-tendon-bone grafts during cruciate ligament reconstruction of the knee. The screw may be made out of a bioabsorbable and/or biocomposite material, i.e. triCalcium phosphate, to allow absorption and enhance bone growth. Other materials of screws may be available in other metals and polymers, such as titanium or TFE, and/or other types of fixation screws may be used.

Another example of a mechanical feature may require incorporating a locking mechanism into the bone block, into the tibial prosthesis, and/or into the tibial bone. A portion of the bone block could be shaped into a dove tail or other arrangement such bone block can be secured to the tibial bone and/or the tibial prosthesis. In various alternative embodiments, the polyethylene spacer could also incorporate features to hold the bone block in place.

Alternatively, the surgeon may determine that the patient requires alignment correction and would like to reposition the bone block to a secondary position for correction. The surgeon may desirably decide to conduct various ranges of motion of the knee to determine the proper tension in both flexion and extension. This technique is similar to a primary ACL reconstruction that is well known in the sports medicine art. Because the bone block and associated ACL should see significant loading, and the loading of the ACL tends to pull the ACL into the knee joint, the tibial component may be pulled upwards and/or anteriorly during flexion and/or extension of the patient's knee.

For example, it may be advantageous for the surgeon to place or reposition the bone block to the anterior aspect of the tibia, or at least a portion of the bone block to the anterior aspect of the tibia in some manner. Once the proper correction or tension is achieved, the surgeon may use any of the bone block cutting guides contemplated herein to create a secondary opening or larger opening where the bone block can be reinserted for correction purposes, desirably restoring and/or preserving the ACL function and alignment. The ACL bone block can be manipulated, wedged, press-fit or otherwise mechanically secured into the secondary anterior cut out of the tibial component, if desired.

To obtain a desired tensioning of the soft tissues including the replaced ACL (and thereby obtain desired kinematics of the repaired joint), the surgeon may perform additional knee balancing after insertion of all implant components and reattachment of the bone block, but before the insertion of one or more tibial spacers. Once desired balancing has been obtained, the appropriate spacer(s) may be introduced. If proper balancing cannot be obtained, the surgeon may elect to reorient and/or reposition the bone block as described herein to alter the tension and/or direction of action of the ACL, and subsequently balance the knee using appropriate spacers.

Figure 15A:
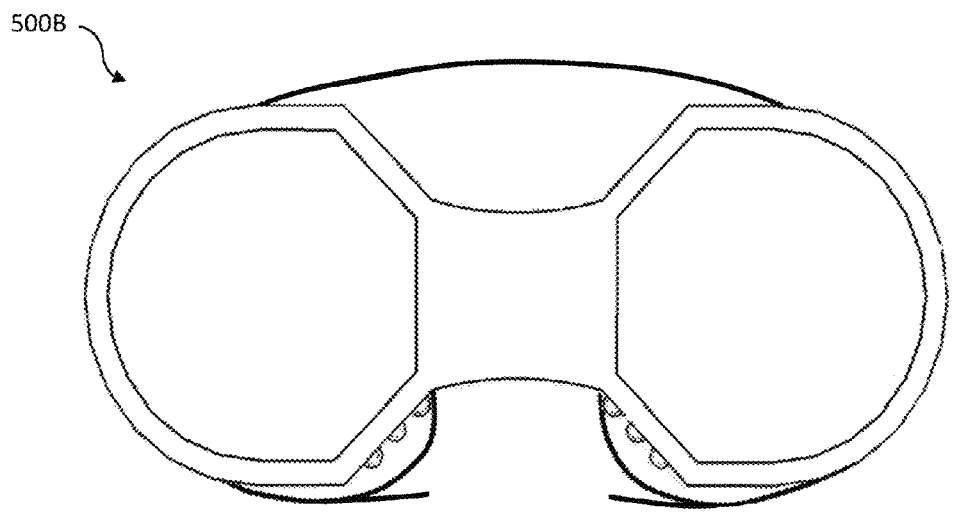
FIGS. 15A and 15B depicts a tibial prosthesis of FIG. 14A placed on a resected tibia and a bone block with the ACL reattached to tibia using a plurality of sutures.
Figure 15B:
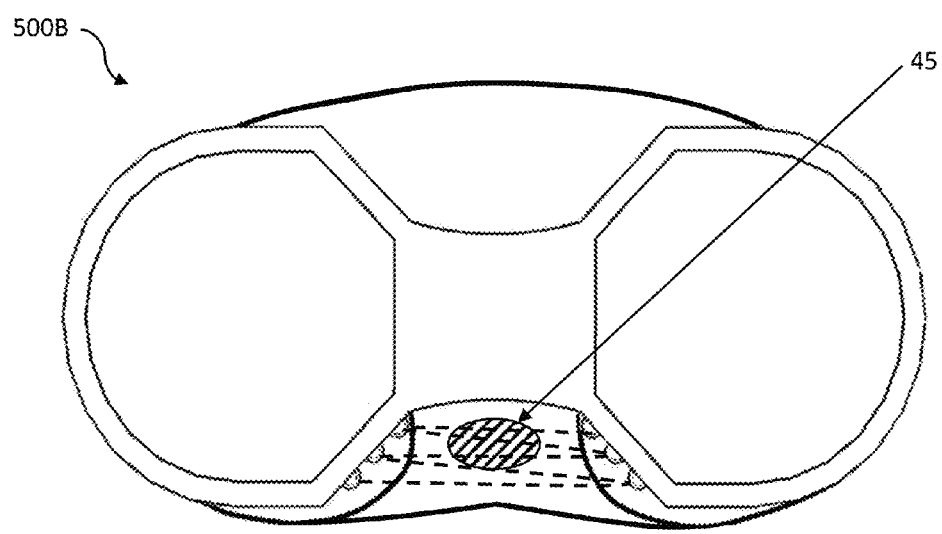
Figure 16A:
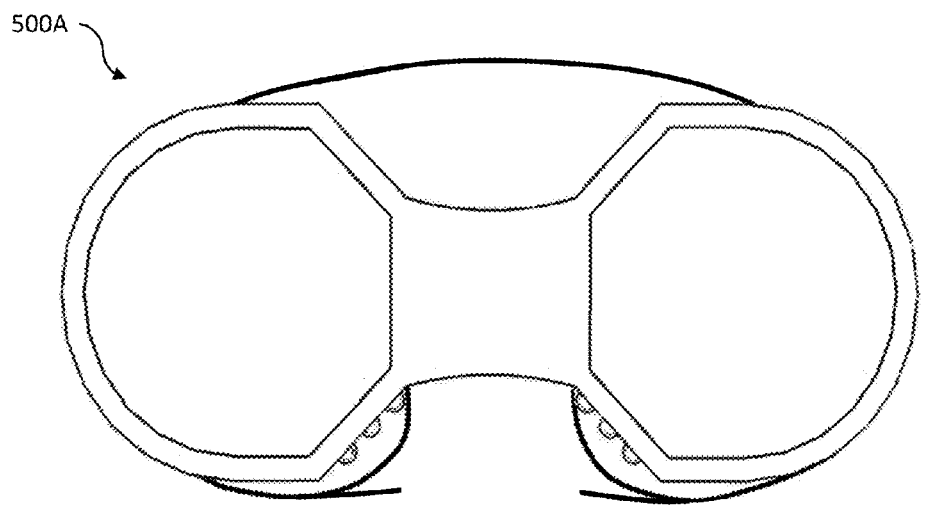
FIGS. 16A and 16B depicts a tibial prosthesis of FIG. 12A placed on a resected tibia and a bone block with the ACL reattached to tibia using a plurality of sutures and securing arm.
Figure 16B:
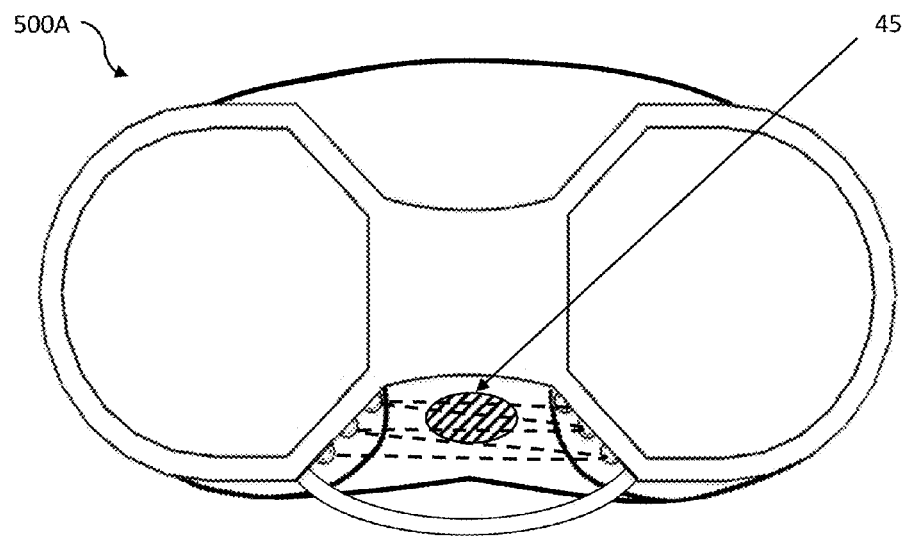

The surgeon may decide to position the tibial prosthesis on the resected tibia after (or potentially prior to) reinsertion of the bone block. The surgeon may use any of the tibial prosthesis contemplated herein to accommodate the bone block. In one embodiment, the surgeon could desirably use a tibial prosthesis with loops and/or anterior metal walls to provide further securement onto the tibia (as shown in FIG. 15 through 17).

Figure 17A:
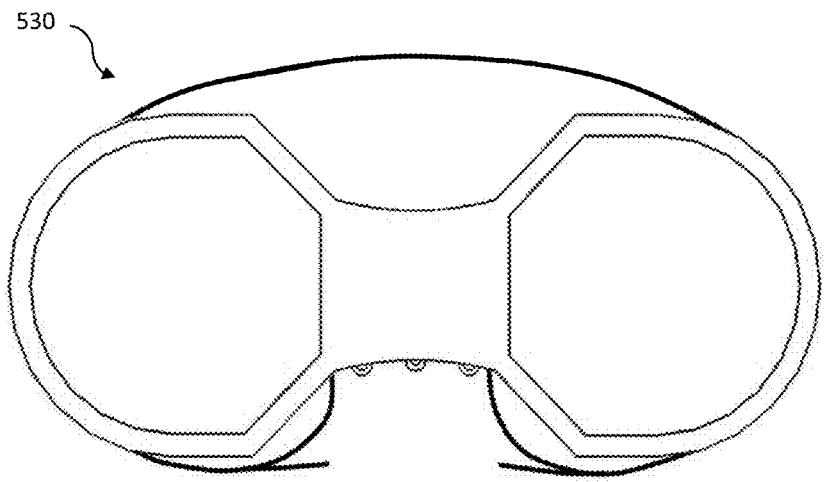
FIGS. 17A and 17B depicts a tibial prosthesis of FIG. 13A placed on a resected tibia and a bone block with the ACL reattached to tibia using a plurality of sutures and securing arm.
Figure 17B:
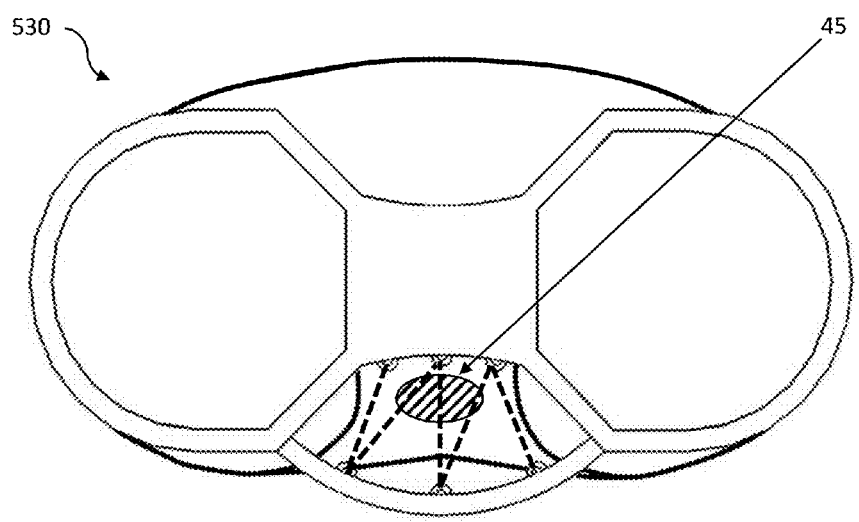

Once the bone block is fastened into place and/or compressed back down on top of the tibial plateau, the surgeon may utilize standard available sutures in the OR to thread through the loops and knot accordingly and/or the manufacturer may decide to pre-load the sutures with the tibial prosthesis if desired. Any type of sutures may be used, such as chromic or plain catgut, polyester, polyethylene, polybutylate, nylon, polydiaoxanone (PDS), polyglactin (Vicryl), polypropylene (Prolene), polyglycolic acid (Dexon), prolene, silk, fibrous materials, metals (i.e. stainless steel), absorbable, non-absorbable, and/or any combinations thereof. Such suture holes could be in the anterior, medial, lateral, and posterior sidewalls of the anterior cut-out and/or in the tibial component. The sutures could be passed through the ACL graft and bone block, be passed over the bone block and around the ACL, and/or passed through the hole out of the anterior cortex on the tibia so the surgeon could tension the bone block with the whole construct in place. The sutures may be placed in a desired orientation based on the desired surgeon's preference, and the design of the tibial tray. The orientation of the sutures may be positioned in the medial-lateral direction (as shown in FIGS. 15A, 15B, 16A and 16B) or anterior-posterior direction (as shown in FIGS. 17A and 17B), or any combination thereof.

In various embodiments, such as where the surgeon may decide to make an adjustment, correction or alignment of the bone block using a secondary anterior cut-out, it may be desirous in various embodiments to include a supplementary fixation feature that anchors the bone block and/or tibial component to the front of the tibia as well as to the resected tibial surface. Such attachment could include plating or screw fixation to the front of tibial, with commensurate securement to one or both of the bone block and/or tibial plate.

In various alternative embodiments, the techniques and system disclosed herein could be used in conjunction with surgical procedures where one or both of the medial portion and/or lateral portion of a tibia might be removed (if desired, using similar cutting tools and techniques). In the disclosed embodiment, the retention of the ACL and PCL, and the associated tension within the knee joint, substantially limits surgical access to the top of the tibia. Accordingly, the cutting of a bone block and "freeing" of the ACL in this manner might facilitate the surgeon's access to the tibia and femur and allow for removal of relevant structures and preparation for the tibial tray implant. If desired, various other cutting tool arrangements, including open-faced guide tools allowing router or rongeur access to the face of the tibia to shape desired surface planes and/or structures, can be utilized.

Any material known in the art can be used for any of the implant, tools, guides and/or systems described in the foregoing embodiments, for example including, but not limited to metal, metal alloys, combinations of metals, plastic, polyethylene, ceramics, cross-linked polyethylene's or polymers or plastics, and biologic materials. In addition, the biologic materials may further include any biocompatible coatings that may assist with the healing response after surgery.

Any fixation techniques and combinations thereof known in the art can be used for any of the implant systems and component described in the foregoing embodiments, for example including, but not limited to cementing techniques, porous coating of at least portions of an implant component, press fit techniques of at least a portion of an implant, ingrowth techniques, etc.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

The invention claimed is:

1. A tibial implant comprising:
    a platform having an upper surface and a bottom surface, the upper surface configured to receive a tibial insert;
    a stem extending downwardly from the bottom surface, the bottom surface contacting the resected proximal tibia; and
    the platform having an anterior portion, a posterior portion and an anterior cut-out formed into the anterior portion of the platform, the platform further including a wall that forms a perimetric portion of the anterior cut-out, the wall extending between the upper surface and the bottom surface of the platform, the wall having a plurality of loops extending outwardly from the wall in a direction away from the posterior portion of the platform.

2. The tibial implant of claim 1, further comprising a posterior cut-out formed into the posterior portion of the platform.

3. The tibial implant of claim 1, further comprising a window.

4. The tibial implant of claim 3, wherein the window substantially matches a shape of a tibial bone portion having an at least one attached ligament.

5. The tibial implant of claim 1, further comprising a non-planar arm extending from a first portion of the platform proximate to a medial portion of the anterior cut-out to a second portion of the platform proximate to a lateral portion of the anterior cut-out.

6. The tibial implant of claim 5, wherein the non-planar arm comprises a plurality of loops extending outward from the non-planer arm towards the posterior portion of the platform.

7. The tibial implant of claim 1, wherein the anterior cut-out substantially matches a shape of a tibial bone portion having an at least one attached ligament.

* * * * *